United States Patent
Sverdlov et al.

(10) Patent No.: US 9,393,303 B2
(45) Date of Patent: Jul. 19, 2016

(54) METHODS FOR TREATING LIVER INFLAMMATION IN A SUBJECT SUFFERING FROM NON-ALCOHOLIC STEATOHEPATITIS

(75) Inventors: Ronit Sverdlov, Maastricht (NL); Veerle Bieghs, Dilsen (BE); Patrick Johannes Jacobus van Gorp, Valkenburg a/d Geul (NL)

(73) Assignees: Universiteit Maastricht, Maastricht (NL); Academisch Ziekenhuis Maastricht, Maastricht (NL)

( * ) Notice: Subject to any disclaimer, the term of this patent is extended or adjusted under 35 U.S.C. 154(b) by 241 days.

(21) Appl. No.: 14/000,850

(22) PCT Filed: Feb. 21, 2012

(86) PCT No.: PCT/EP2012/052918
§ 371 (c)(1), (2), (4) Date: Oct. 24, 2013

(87) PCT Pub. No.: WO2012/113783
PCT Pub. Date: Aug. 30, 2012

(65) Prior Publication Data
US 2014/0044734 A1    Feb. 13, 2014

(30) Foreign Application Priority Data
Feb. 21, 2011 (EP) .................................... 11155267

(51) Int. Cl.
| | | |
|---|---|---|
| A61K 39/00 | (2006.01) | |
| A61K 39/395 | (2006.01) | |
| A61K 39/02 | (2006.01) | |
| A61K 39/09 | (2006.01) | |
| A61P 1/16 | (2006.01) | |
| C07K 16/18 | (2006.01) | |
| C07K 16/12 | (2006.01) | |

(52) U.S. Cl.
CPC ....... *A61K 39/39575* (2013.01); *A61K 39/0005* (2013.01); *A61K 39/0012* (2013.01); *A61K 39/0013* (2013.01); *A61K 39/092* (2013.01); *A61K 39/3955* (2013.01); *C07K 16/1275* (2013.01); *C07K 16/18* (2013.01); *A61K 2039/505* (2013.01); *A61K 2039/521* (2013.01); *A61K 2039/55566* (2013.01)

(58) Field of Classification Search
None
See application file for complete search history.

(56) References Cited

FOREIGN PATENT DOCUMENTS

| WO | WO 2004/091520 A2 | 10/2004 |
| WO | WO 2012/113783 A1 | 8/2012 |

OTHER PUBLICATIONS

Bieghs et al, 2010. Gastroenterology. 138(7): 2477-2486.*
Bieghs et al. 2013. Hepatology. 56(3): 894-903.*
PCT International Preliminary Report on Patentability, PCT/EP2012/052918 dated Aug. 21, 2013.
Kang et al., Curcumin eliminates oxidized LDL roles in activating hepatic stellate cells by Suppressing Gene Expression of Lectin-like oxidized LDL receptor-1, Laboratory Investigation, Nov. 2009, pp. 1275-1290, vol. 89, No. 11.
Binder et al., Pneumococcal vaccination decreases atherosclerotic lesion formation: molecular mimicry between *Streptococcus* pneumonia and oxidized LDL, Nature Medicine, Jun. 1, 2003, pp. 736-743, vol. 9, No. 6.
PCT International Search Report and Written Opinion, PCT/EP2012/052918, dated Apr. 12, 2012.

\* cited by examiner

*Primary Examiner* — Zachary Howard
(74) *Attorney, Agent, or Firm* — TraskBritt, P.C.

(57) ABSTRACT

The invention is in the field of prevention and medical treatment of liver diseases, in particular non-alcoholic steatohepatitis (NASH). The invention provides means and methods for the treatment of hepatic inflammation, fibrosis and more in particular NASH. More in particular, the invention provides a composition capable of raising anti-oxLDL antibodies in vivo for use in the treatment of liver inflammation or fibrosis.

11 Claims, 26 Drawing Sheets

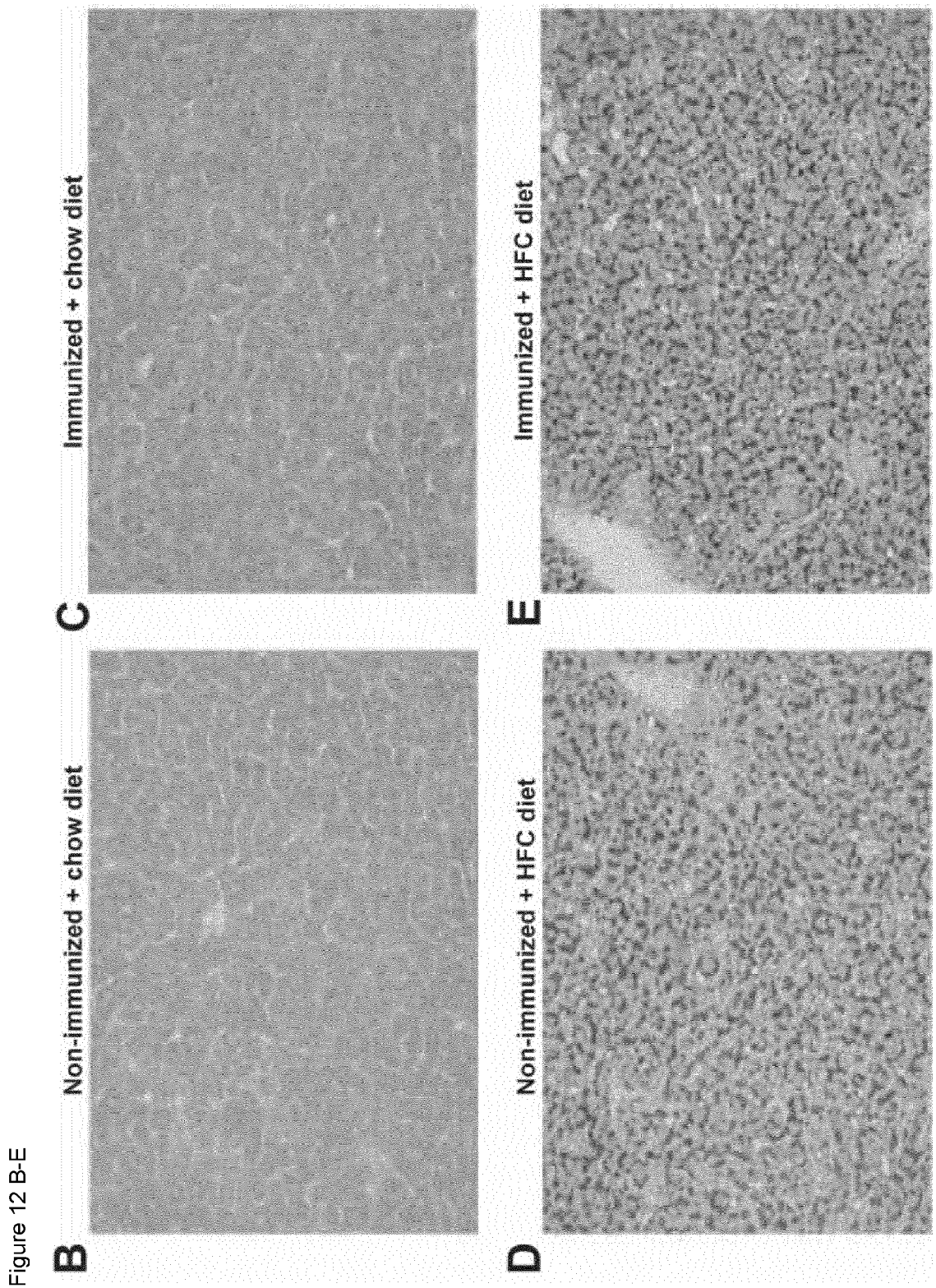
Figure 12 B-E

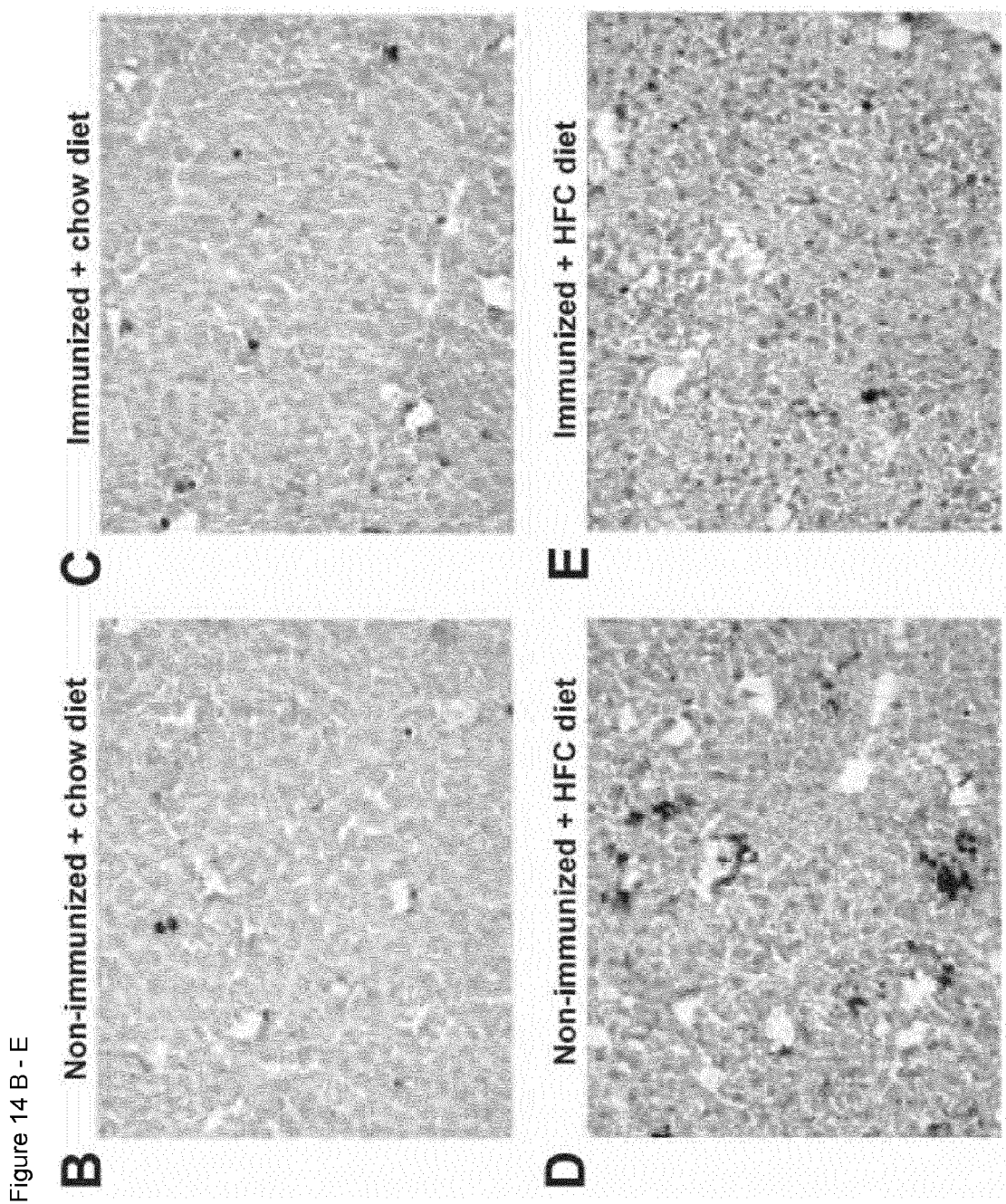
Figure 14 B - E

Figure 16C:
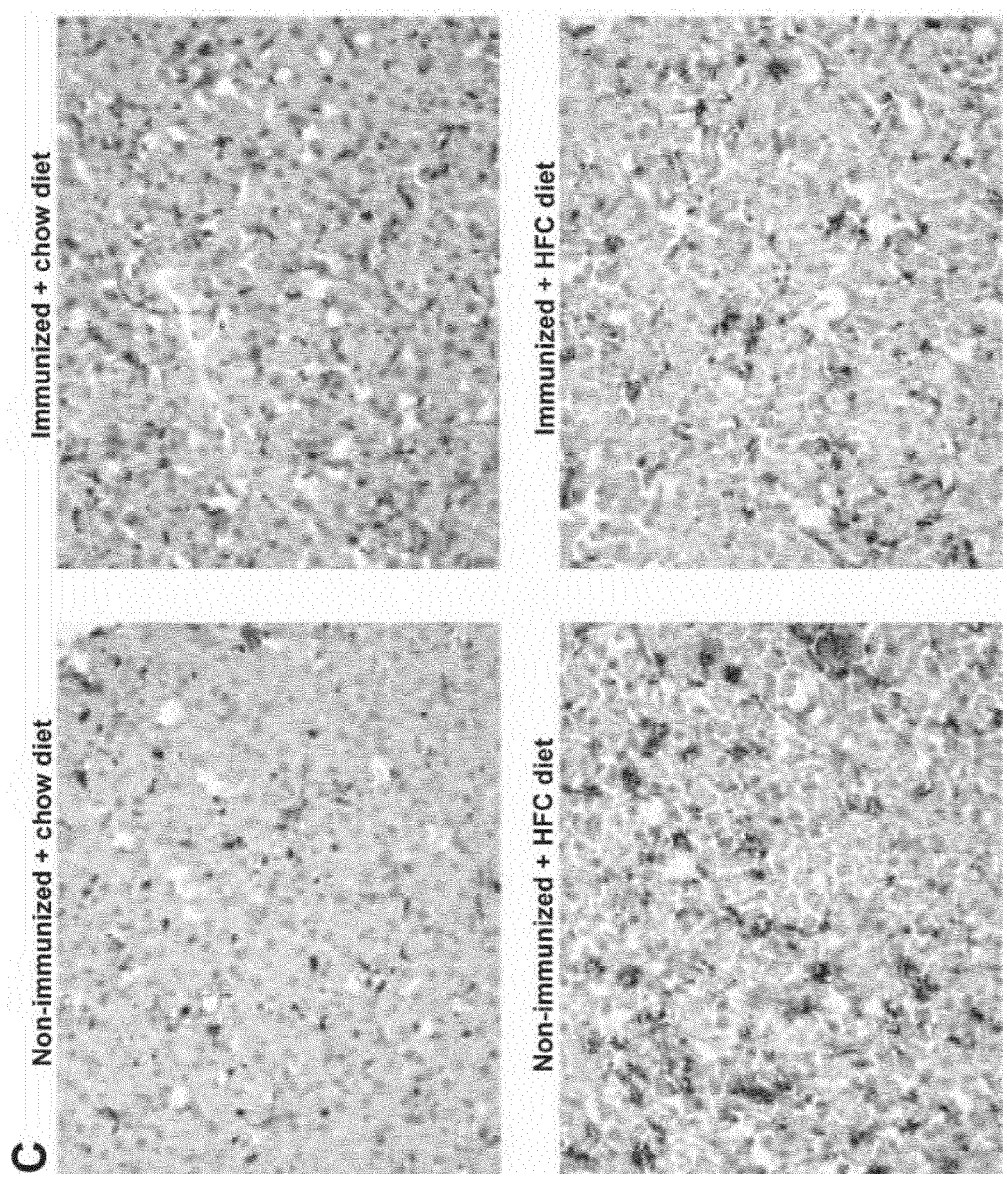

Figure 16A and B
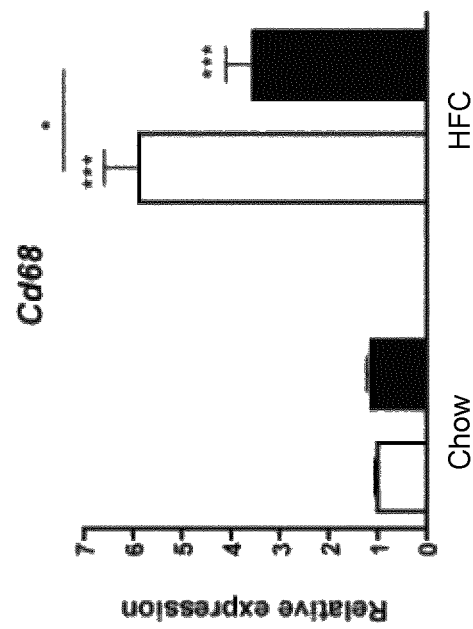
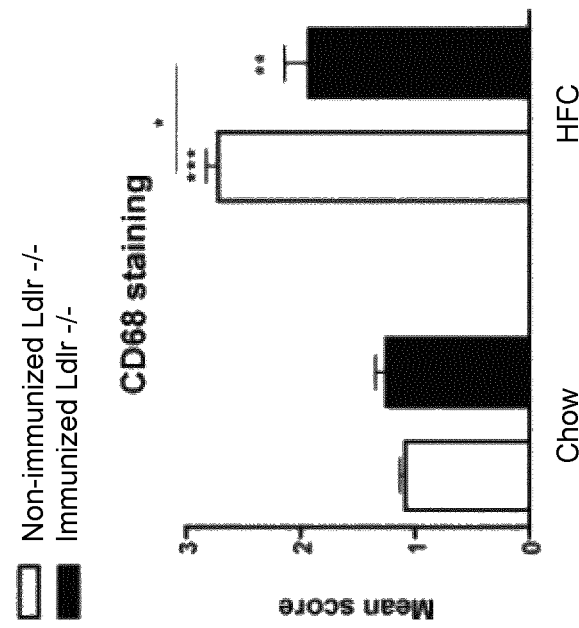

METHODS FOR TREATING LIVER INFLAMMATION IN A SUBJECT SUFFERING FROM NON-ALCOHOLIC STEATOHEPATITIS

FIELD OF THE INVENTION

The invention is in the field of prevention and medical treatment of liver diseases, such as liver inflammation, fibrosis and more in particular non-alcoholic steatohepatitis.

BACKGROUND OF THE INVENTION

Non-alcoholic fatty liver disease (NAFLD) is a condition ranging from benign lipid accumulation in the liver (steatosis) to steatosis combined with inflammation. The latter is referred to as non-alcoholic steatohepatitis (NASH). NASH is viewed as the hepatic component of metabolic syndrome. Estimates from the USA are that 5.7% to 17% of all adults have NASH, while 17% to 33% of Americans have NAFLD [1, 2]. As obesity and insulin resistance reach epidemic proportions in industrialized countries, the prevalence of both NAFLD and NASH is increasing and is therefore considered to be a major health hazard [3]. Steatosis alone is considered a relatively benign condition for the liver itself and is also a reversible condition However, the transition towards NASH represents a key step in the pathogenesis, as it sets the stage for further damage to the liver, such as fibrosis, cirrhosis and liver cancer. While the mechanisms leading to steatosis are well described, little is known about the actual risk factors that drive hepatic inflammation during the progression to NASH. Consequently, therapeutic options are poor.

Currently, liver biopsy is used in the clinical practice as the primary method for detection of liver inflammation in NASH.

There is no established therapy for patients suffering from NASH. Therapy is, therefore, focused mainly on risk factors, weight reduction and pharmacological intervention. Promising pharmacological treatments have been demonstrated with antioxidants, insulin sensitizers, hepatoprotectants and lipid-lowering agents.

It is an object of the present invention to provide an alternative therapy for NASH.

SUMMARY OF THE INVENTION

We found that NASH may be treated or prevented by raising the level of antibodies against oxidized LDL (anti-oxLDL) in patients with NASH. For this we used a model system employing Ldlr−/− mice fed with a high fat cholesterol diet (HFC diet) against a control group of the same mice fed with a normal Chow diet. This model is accepted in the art to adequately reflect NASH.

Severity of NASH and disease progression may be determined by measuring hepatic inflammation. Such may be done by studying the expression of genes indicative for hepatic inflammation. Such genes are known in the art. Hepatic inflammation may be taken as a measure of disease severity and progression. Hepatic inflammation may also be determined by immunohistochemistry.

Both of these inflammation parameters are shown herein to be lowered upon treatment with a composition capable of increasing the level of anti-oxLDL antibodies. Hence, anti-oxLDL may effectively be used in the treatment of NASH. In particular anti-oxLDL antibodies of the IgM class were found to be effective.

The invention therefore relates to a composition comprising antibodies against oxLDL for use in the treatment or prevention of NASH.

Alternatively, such antibodies may also be generated in a patient in vivo in an active immunization procedure. Therein, a composition capable of increasing the level of anti-oxLDL antibodies is administered to a patient. Upon this immunization, the patient's immune system reacts with anti-oxLDL antibodies, in particular of the IgM class. Compositions capable of raising anti-oxLDL antibodies are known in the art and share the common structural feature of a phosphorylcholine (PC) headgroup or determinant.

Phosphorylcholine headgroups or determinants or epitopes are known in the art and may be structurally defined as a structure according to formula 1:

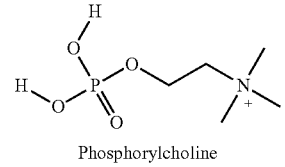

Phosphorylcholine

Formula 1

The invention therefore also relates to a composition capable of increasing the level of anti-oxLDL antibodies in vivo for use in the treatment or prevention of NASH. Particularly suitable compositions are those comprising a PC headgroup. A particularly preferred composition is a composition comprising antigens derived from *Streptococcus*, such as *S. pneumoniae*. Such antigens may be advantageously obtained by heat-inactivating *Streptococcus pneumonia*.

Upon oxidation of LDL, reactive oxidation products from phospholipids retain the intact phosphorylcholine (PC) headgroup. These PC headgroups are called 'oxidation-specific' epitopes and are found on the outer side of the membrane, triggering an innate immune response [15].

A panel of monoclonal autoantibodies directed to epitopes of oxLDL was recently cloned from the spleen of apoE−/− mice [16]. In particular, one immunodominant clonotypic set of IgM autoantibodies was identified, EO6, which bears the T15 idiotype and which was shown to specifically bind to the PC moiety of oxidized PC-containing phospholipids, such as those present in oxLDL [15].

Interestingly, a remarkable resemblance between EO6 antibodies and the natural T15 antibodies from the B-1 cell clone was found. These T15 antibodies, which are known to protect mice against *Streptococcus pneumoniae* infections, recognize the same epitope present on oxLDL since the cell wall of this bacterium consists of the same PC headgroup. Accordingly, by immunizing Ldlr−/− mice with *S. pneumoniae*, higher titers of serum anti-oxLDL antibodies were measured. In addition, increased IgM immune complexes with apoB-containing particles were found in the plasma of these Ldlr−/− mice immunized with *S. pneumoniae*, suggesting that IgM antibodies bind oxLDL specifically. These findings show that anti-oxLDL antibodies are directed to the PC headgroup present on oxLDL.

DETAILED DESCRIPTION OF THE INVENTION

Ldlr−/− mice fed with a HFC diet were employed as a model system for the treatment or prevention of NASH. AntioxLDL antibodies were elicited by challenging the immune system with PC-headgroup comprising molecules such as *S. pneumoniae*.

Figure 1:
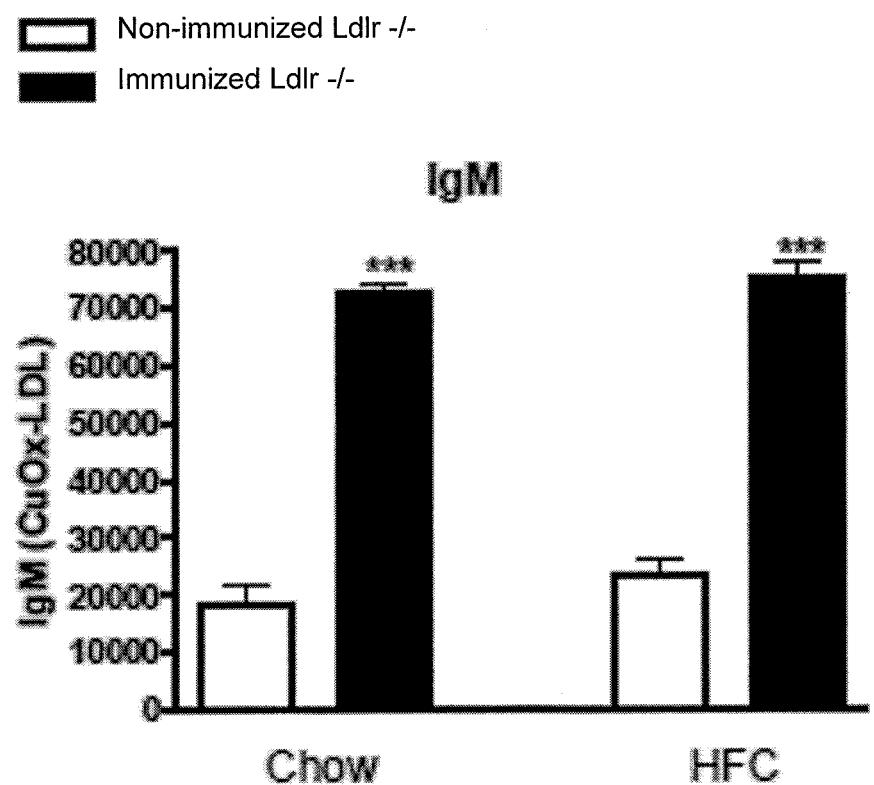

Immunization of Ldlr-/- mice with heat-inactivated *S. pneumoniae* resulted in a strong increase in titers of IgM antibodies against oxLDL in plasma, which was not observed in non-immunized Ldlr-/- mice (FIG. 1). These experiments show that anti-oxLDL antibodies may effectively be generated by challenging the immune system with a composition comprising a compound comprising a PC headgroup.

Figure 2:
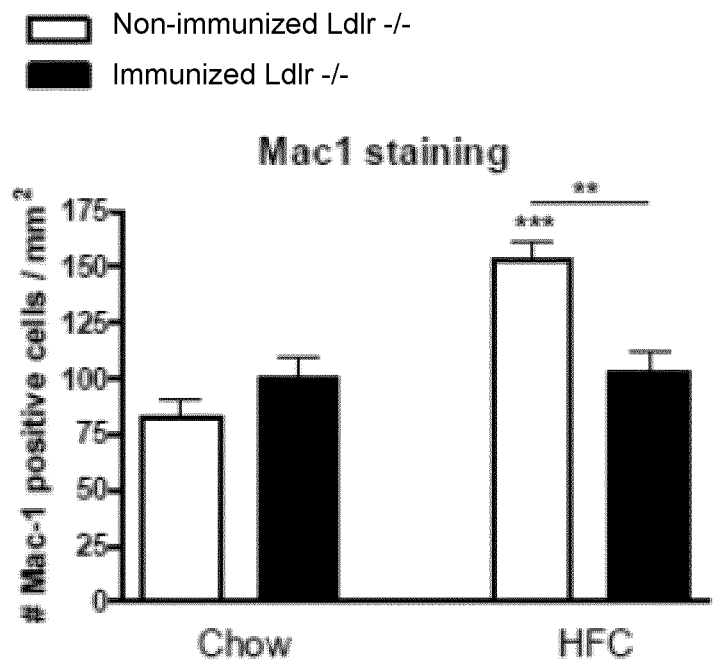
Figure 2:
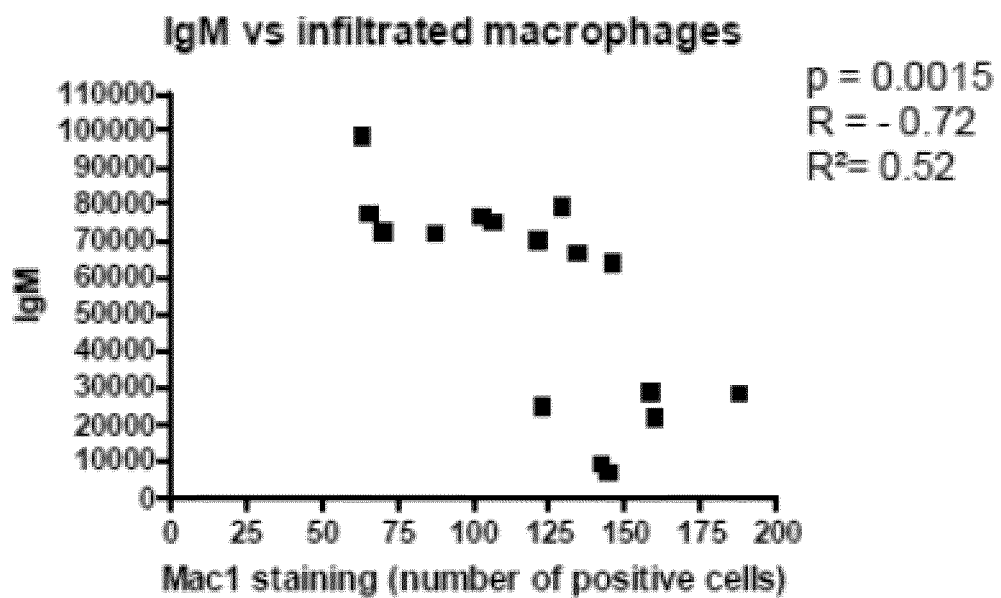
Figure 3:
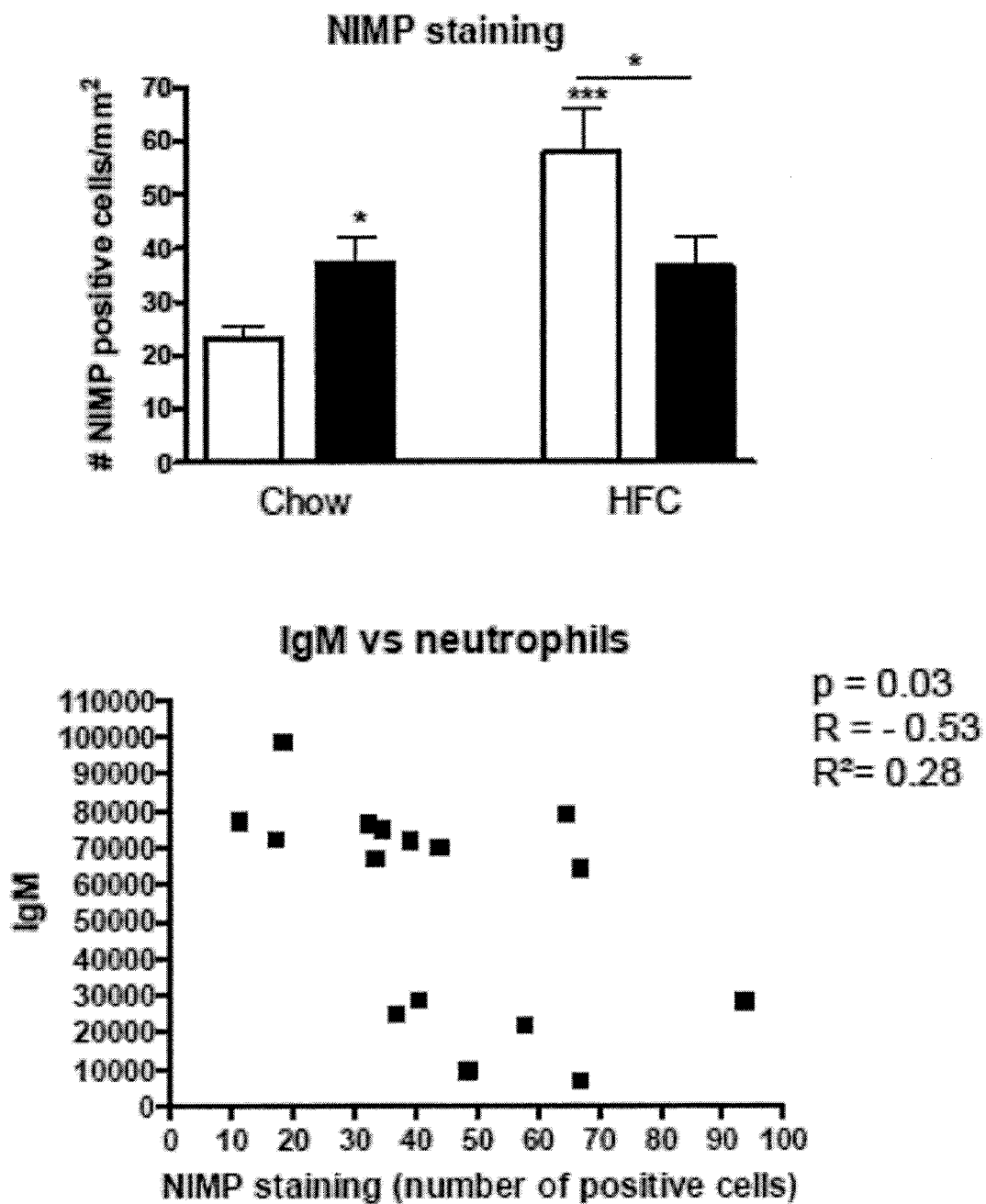
Figure 4:
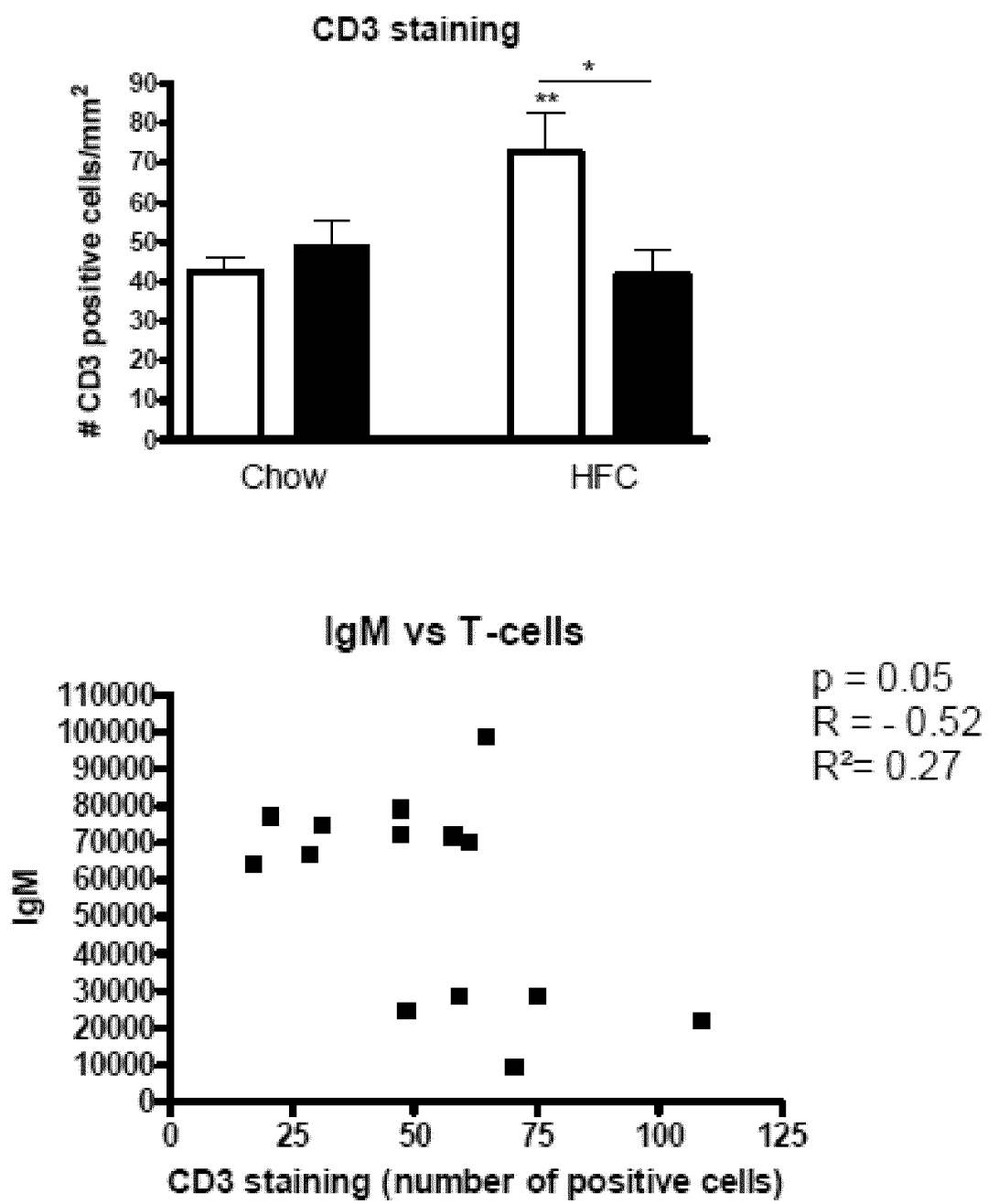

To determine whether immunization of Ldlr-/- mice with heat-inactivated *S. pneumoniae* affects or prevents hepatic inflammation, liver sections were stained for the inflammatory cell markers Mac-1 (infiltrated macrophages and neutrophils), NIMP (neutrophils) and CD3 (T cells). As shown in FIGS. 2-4, the amount of infiltrated macrophages, neutrophils and T cells was lower in immunized Ldlr-/- mice compared to non-immunized mice after feeding on the HFC diet.

It may therefore be concluded that immunization with a composition comprising a compound comprising a PC headgroup reduces the number of inflammatory cells in a model system for NASH. A compound comprising a PC headgroup may therefore effectively be employed for reducing or preventing liver inflammation which may be particularly useful in the treatment of NASH. Also, oxLDL antibodies may be employed for that purpose, in particular IgM anti-oxLDL antibodies.

This conclusion is further corroborated by analysis of liver gene expression. This showed a significant decrease in the inflammatory markers tumour necrosis factor (Tnf), interleukin-1beta (Il-1b), interleukin 6 (Il-6) and monocyte chemoattractant protein-1 (Mcp1) in immunized Ldlr-/- mice on the HFC diet compared to non-immunized mice (FIGS. 5-8)

Figure 9:
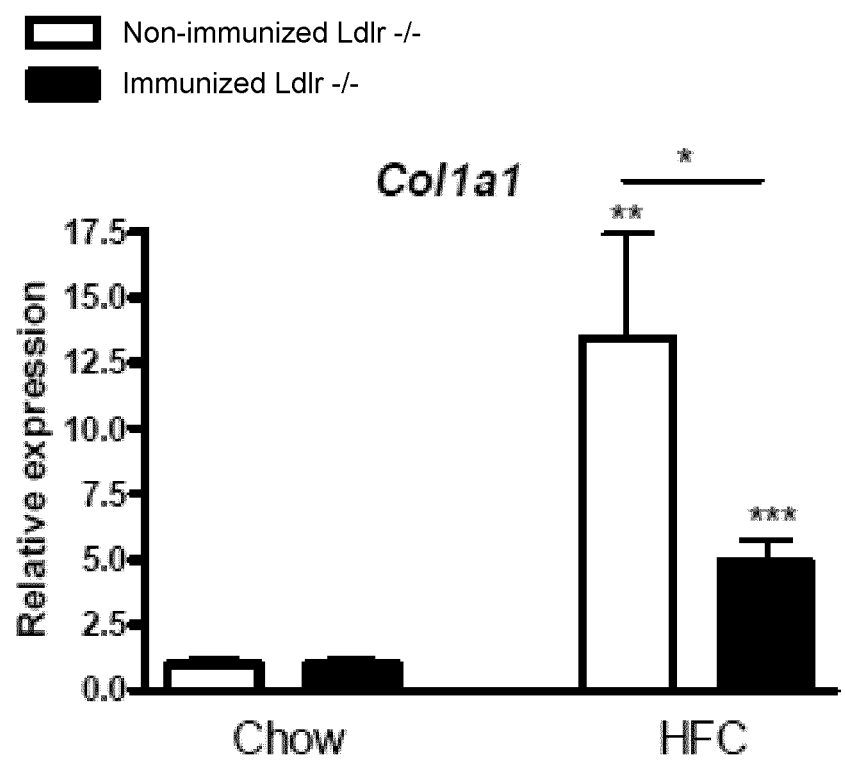
Figure 10:
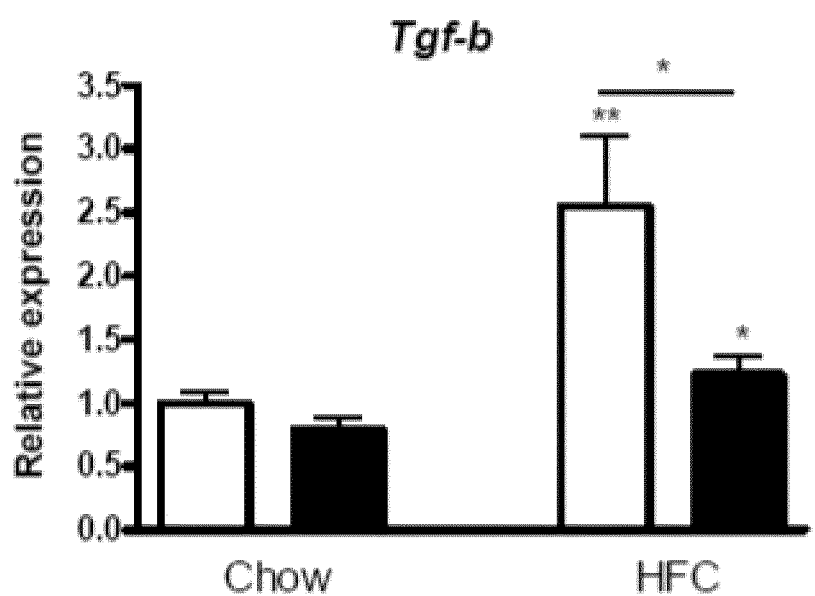

Fibrosis is considered to be an advanced stage of NASH. Gene expression analysis for collagen type 1A1 (Col1A1) and transforming growth factor beta (Tgf-β) indicated that the mRNA levels of these genes were lower in immunized mice compared to non-immunized mice on the HFC diet (FIGS. 9 and 10).

These experiments show that immunization with a compound comprising a PC headgroup may effectively be used to treat or prevent fibrosis, more in particular fibrosis in NASH patients. Antibodies against oxLDL may therefore also be employed in a passive immunization scheme. In such a scheme, IgM anti-oxLDL antibodies are preferred.

Until now, the actual risk factors that drive hepatic inflammation during the progression to NASH have been unknown. In the experiments as described herein we have shown that hepatic inflammation and fibrosis may be dramatically decreased or prevented by increasing serum anti-oxLDL antibody levels. This may be done by any method currently known in the art, advantageously as exemplified herein with heat-inactivated *S. pneumonia*. These data suggest that oxLDL may be a trigger for hepatic inflammation. Irrespective of the mechanism that causes hepatic inflammation in general or hepatic inflammation in NASH in particular, our data show that oxLDL antibodies may effectively be used in order to combat or prevent hepatic inflammation, in particular in the treatment of NASH.

Antibodies against oxLDL are known in the art. The invention relates to a new medical use of such antibodies. In other words, the invention relates to a composition comprising antibodies against oxLDL for use in the treatment or prevention of hepatic inflammation or more in particular the treatment or prevention of NASH. Yet in other words, the invention relates to the use of oxLDL antibodies for the preparation of a medicament for the treatment or prevention of hepatic inflammation, more in particular the treatment or prevention of NASH.

Such antibodies may also be raised in vivo in a patient in need of such a treatment. Compositions capable of increasing the level of anti-oxLDL antibodies in plasma are known in the art. The invention therefore relates to a new medical use of such a composition in the treatment or prevention of hepatic inflammation or NASH. In other words, the invention relates to a composition capable of raising anti-oxLDL antibodies in vivo for use in the treatment or prevention of hepatic inflammation, more in particular in the treatment or prevention of NASH. In yet another wording, the invention relates to the use of a composition capable of raising anti-oxLDL antibodies in plasma for the manufacture of a medicament for the treatment or prevention of hepatic inflammation more in particular for the treatment or prevention of NASH.

Antibodies against oxLDL may effectively be raised in vivo by immunization of an individual in need of such a treatment with a composition comprising a PC headgroup.

The invention therefore relates to a composition for use as described above wherein the composition comprises a compound comprising a PC headgroup.

Yet in other words, the invention relates to a method of treatment or prevention of hepatic inflammation in a patient in need of such a treatment wherein the level of circulating oxLDL antibodies is increased. Such may be accomplished by passive immunization with a vaccine comprising oxLDL antibodies. Such a vaccine may additionally comprise at least one adjuvant and/or a pharmaceutically acceptable carrier. Increasing the level of anti-oxLDL antibodies may also be accomplished by immunizing a patient in need thereof with a composition capable of raising anti-oxLDL antibodies in vivo. Such a composition may advantageously comprise a compound comprising a PC headgroup, such as *S. pneumonia*, in particular heat inactivated *S. pneumonia*.

In summary, our data demonstrate that inflammation is reduced in the livers of heat-inactivated *S. pneumoniae*-immunized mice.

As fibrosis is one of the later consequences of NASH, we also investigated the effect of immunization with heat-inactivated *S. pneumoniae* on hepatic fibrosis. In agreement with the above findings, we found that gene expression of fibrosis-related genes was decreased. It may therefore be concluded that oxLDL plays an important role in hepatic inflammation and fibrosis and therefore contribute to the pathogenesis of NASH. Anti-oxLDL antibodies may therefore be successfully employed in the treatment or prevention of liver inflammation, more in particular in the treatment or prevention of NASH.

By investigating the IgM antibody titers against oxLDL in human NASH patients, we observed that these titers were reduced in NASH patients compared to subjects with a healthy liver or steatosis alone. These data show that oxLDL acts as a trigger for hepatic inflammation. Furthermore, we have shown that PC-based vaccines may be used in a vaccination protocol towards the therapy or prevention of NASH in humans.

Similarly, apoE-/- mice immunized with PC headgroups, one of the epitopes of anti-oxLDL autoantibodies present in oxLDL but also in the CPS of *S. pneumoniae*, demonstrated an increase in anti-oxLDL autoantibodies together with a reduction in atherosclerotic lesions (75).

Importantly, we showed that the protective IgM levels against oxLDL in plasma are lower in NASH patients compared to subjects with a healthy liver or steatosis.

LEGEND TO THE FIGURES

FIG. 1: Immunization with S. pneumonia induces IgM antibodies against oxLDL.

FIG. 2: Macrophages are significantly reduced in a NASH model system upon immunization with oxLDL antibodies. Liver sections were stained for infiltrated macrophages (Mac-1), and counted. Lower panel shows the negative correlation between IgM anti-oxLDL antibodies and macrophages.

FIG. 3: Neutrophils are significantly reduced in a NASH model system upon immunization with oxLDL antibodies. Liver sections were stained for infiltrated neutrophils (NIMP) and counted. Lower panel shows the negative correlation between IgM anti-oxLDL antibodies and neutrophils.

FIG. 4: T-cells are significantly reduced in a NASH model system upon immunization with oxLDL antibodies. Liver sections were stained for infiltrated T cells (CD3) and counted. Lower panel shows the negative correlation between IgM anti-oxLDL antibodies and T cells.

Figure 5:
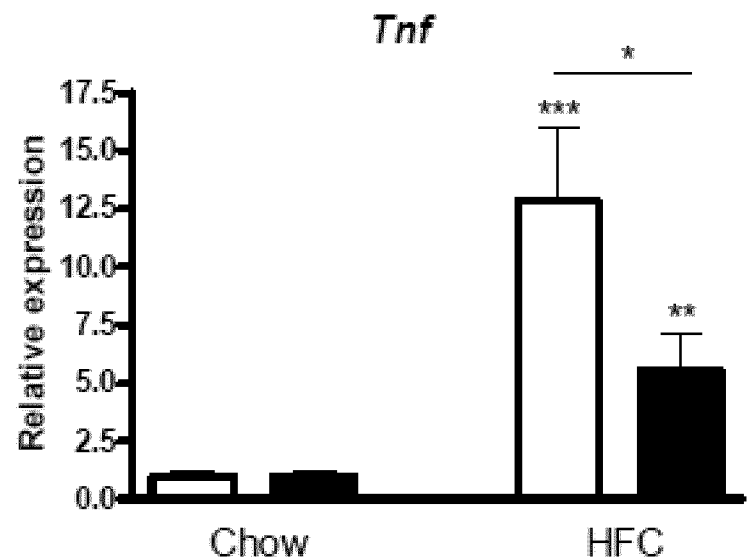
Figure 5:
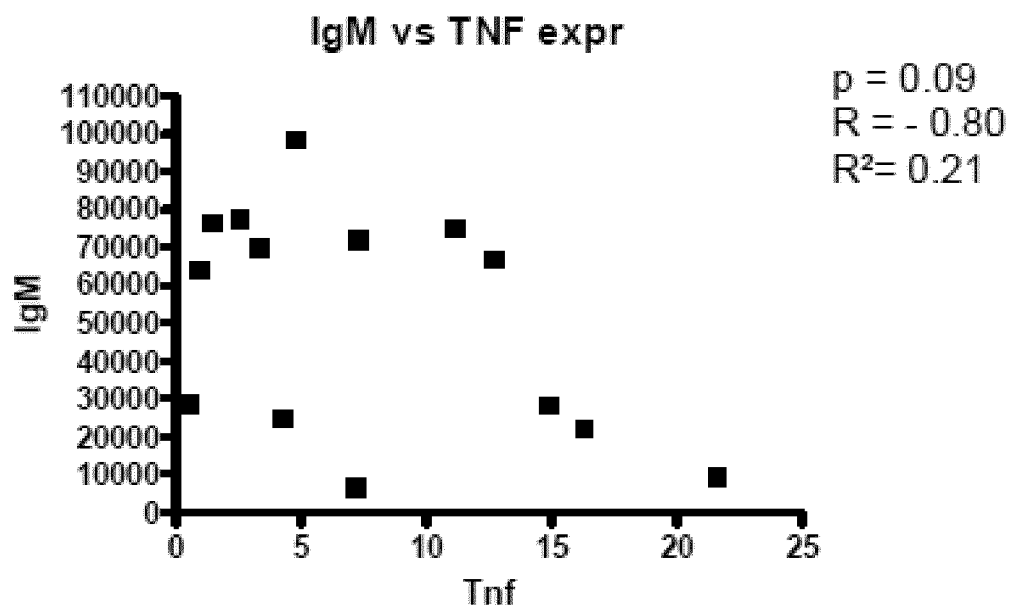

FIG. 5 Gene expression analysis for tumour necrosis factor (Tnf). * Significantly different from the mice on chow diet. *,  and * indicate $p<0.05$, 0.01 and 0.001 respectively. Lower panel shows the negative correlation between IgM anti-oxLDL antibodies and Tnf.

Figure 6:
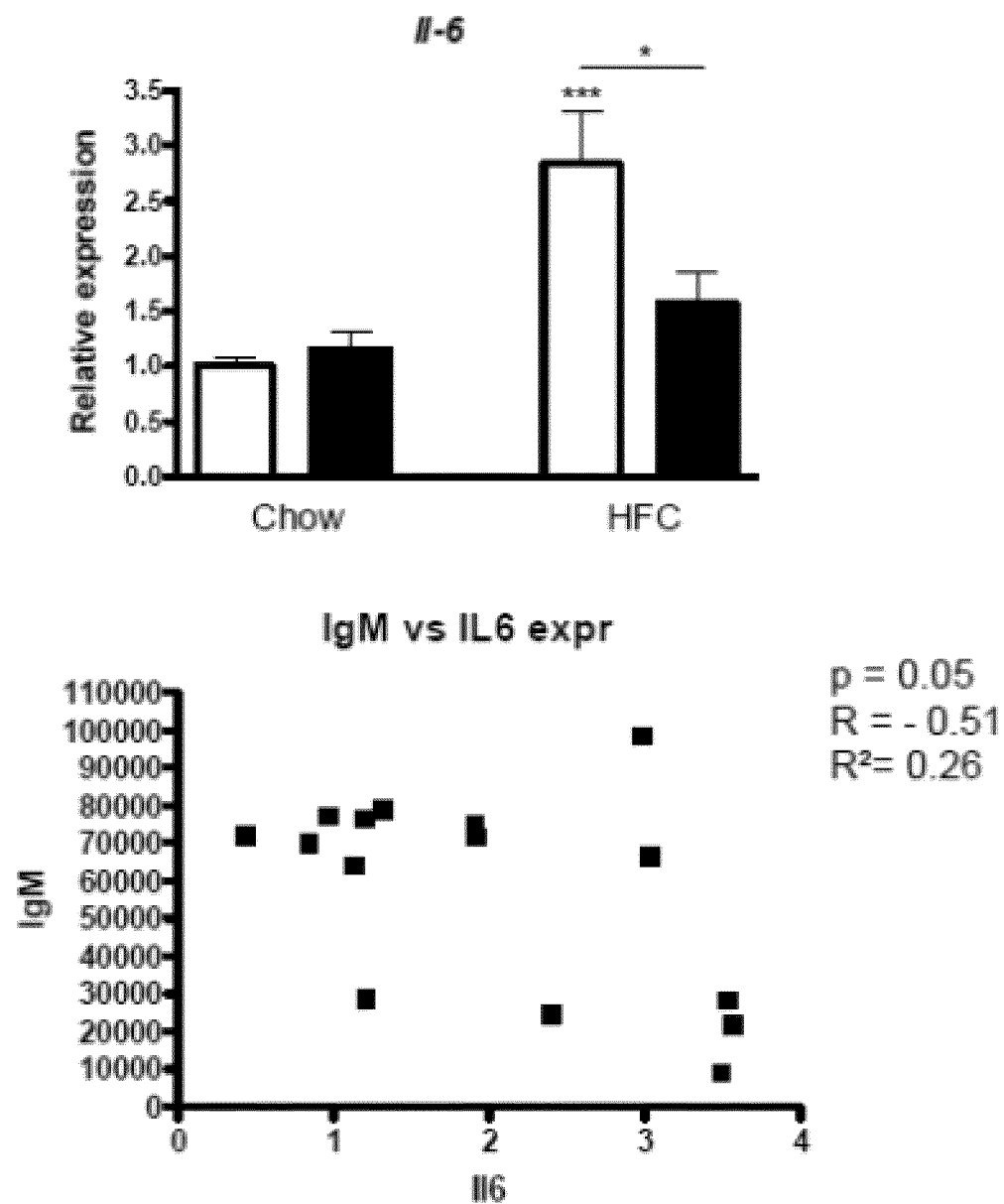

FIG. 6 Gene expression analysis for interleukin 6 (Il6). * Significantly different from the mice on chow diet. *,  and * indicate $p<0.05$, 0.01 and 0.001 respectively. Lower panel shows the negative correlation between IgM anti-oxLDL antibodies and interleukin 6.

Figure 7:
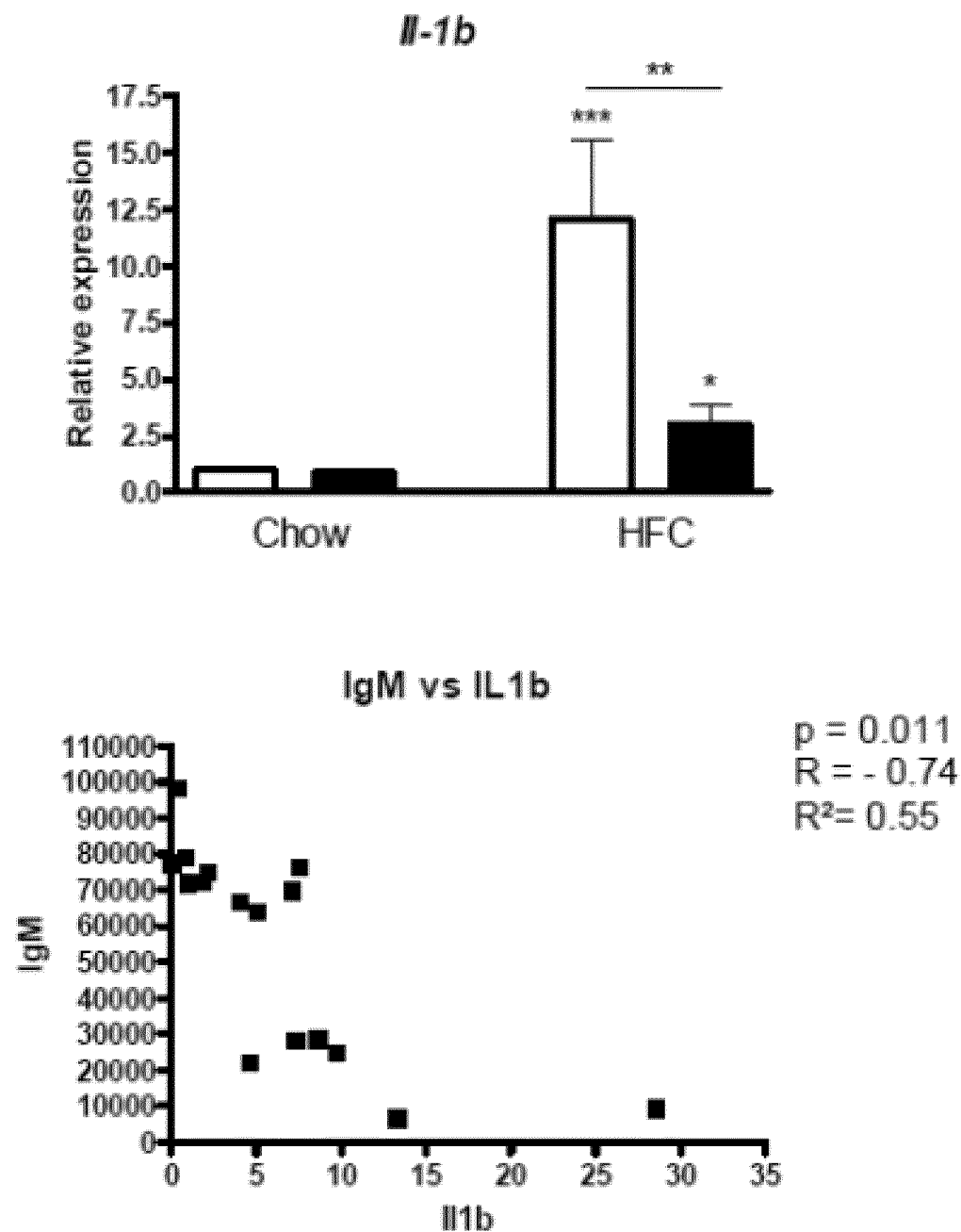

FIG. 7 Gene expression analysis for interleukin 1β (Il1β). * Significantly different from the mice on chow diet. *,  and * indicate $p<0.05$, 0.01 and 0.001 respectively. Lower panel shows the negative correlation between IgM anti-oxLDL antibodies and interleukin 1β.

Figure 8:
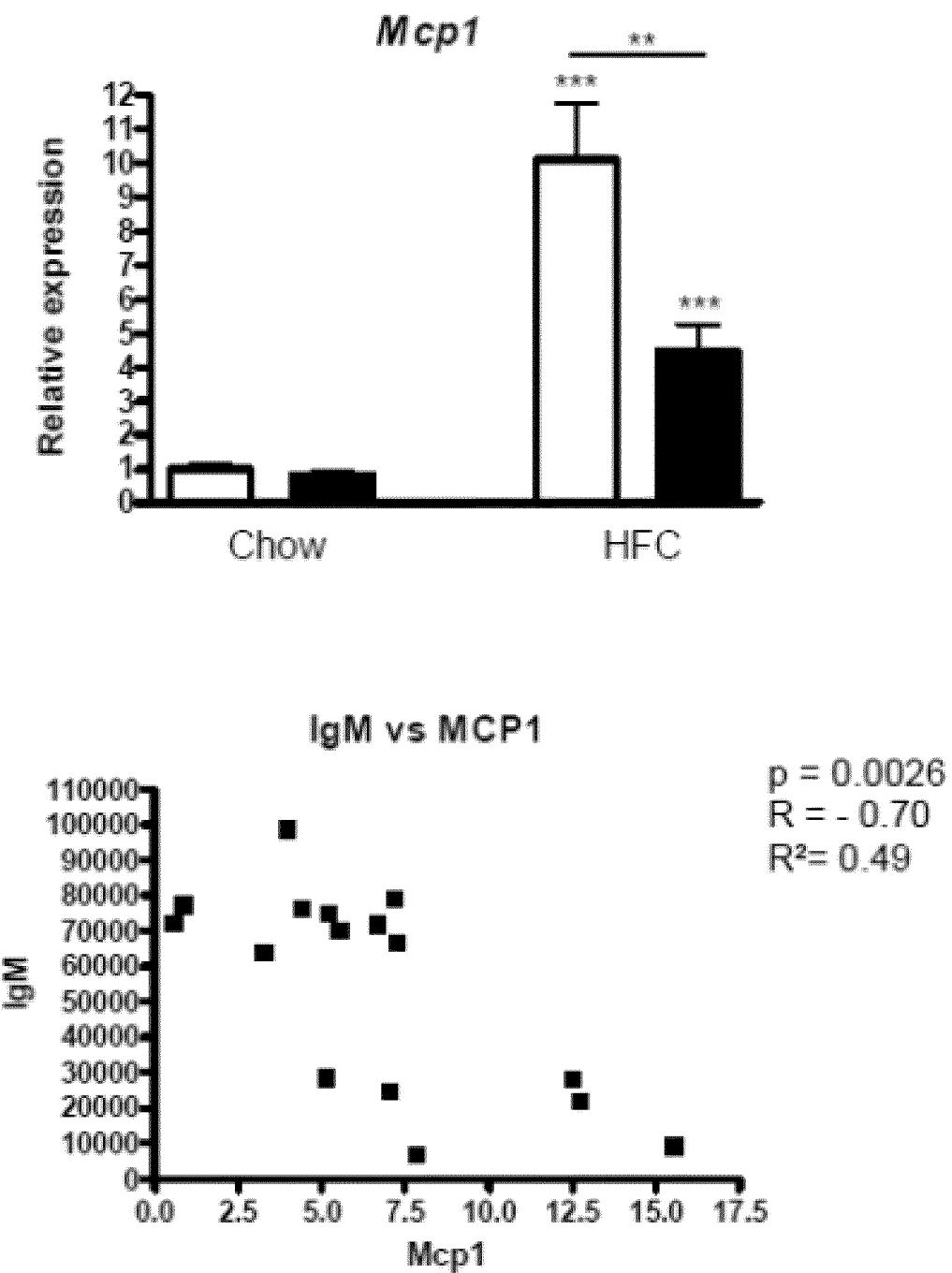

FIG. 8 Gene expression analysis for monocyte chemoattractant protein 1 (Mcp1). * Significantly different from the mice on chow diet. *,  and * indicate $p<0.05$, 0.01 and 0.001 respectively. Lower panel shows the negative correlation between IgM anti-oxLDL antibodies and monocyte chemoattractant protein 1 (Mcp1).

FIG. 9 Gene expression analysis of the fibrosis marker collagen (Col1a1). * Significantly different from the mice on chow diet. *,  and * indicate $p<0.05$, 0.01 and 0.001 respectively.

FIG. 10 Gene expression analysis of the fibrosis marker transforming growth factor beta (Tgf-β). * Significantly different from the mice on chow diet. *,  and * indicate $p<0.05$, 0.01 and 0.001 respectively.

Figure 11:
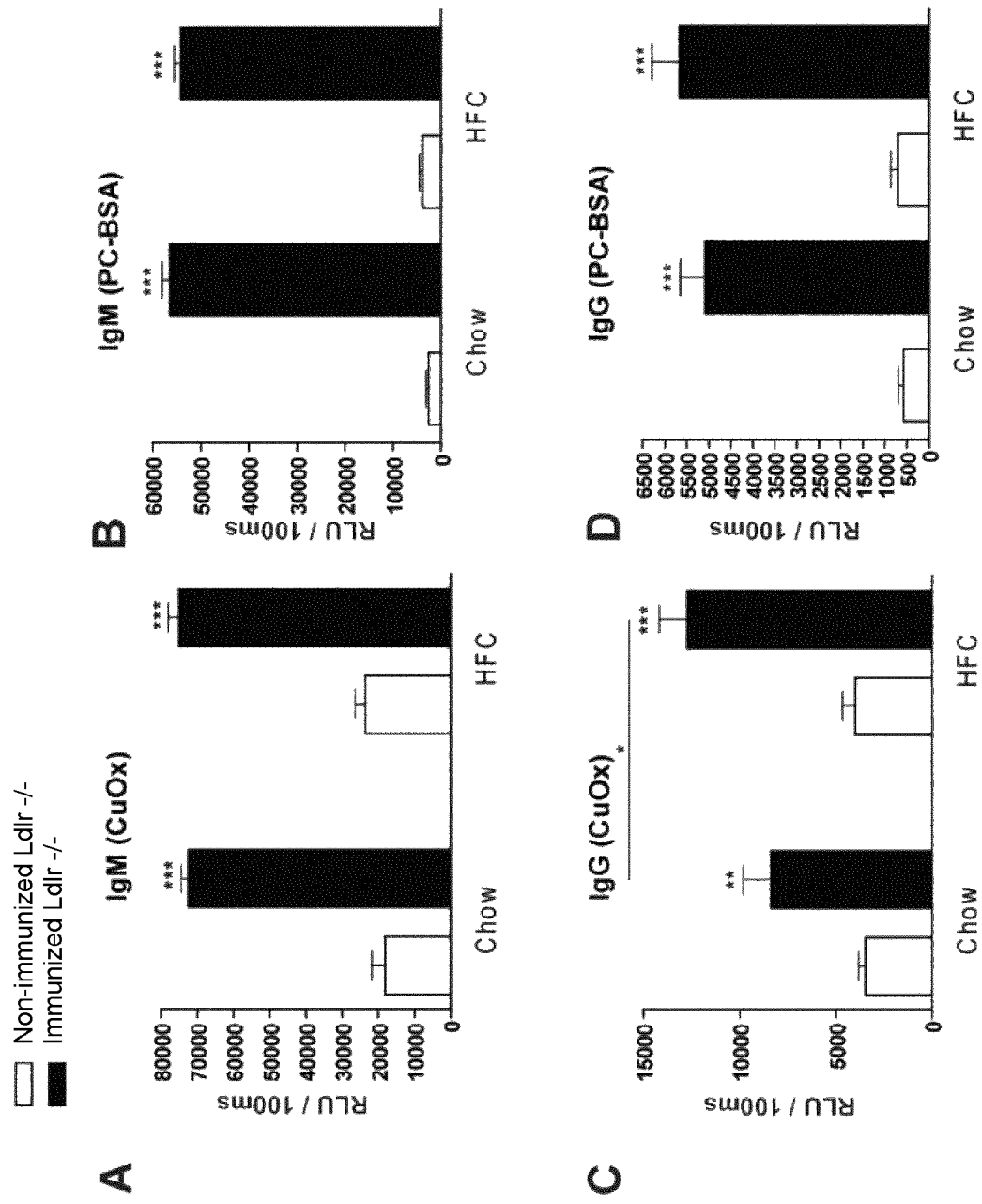

FIG. 11: IgM autoantibodies in mice that received pneumococcal immunization. (A-D) IgM and IgG antibodies against oxLDL (CuOx and PC-BSA) were measured in plasma of pneumococci-immunized (n=10) and control (n=10) mice at a dilution of 1:200, respectively. Data is expressed as RLU=Relative light units/100 ms and were triplicate determinations. (*,  and *: $p<0.05$; 0.01; 0.001 respectively).

FIG. 12: Liver lipid levels. (A) Liver cholesterol, triglycerides (TG) and free fatty acids (FFA) after chow and 3 weeks of HFC diet. (B-E) Oil red O staining after 3 weeks of HFC diet in (B+D) non-immunized (C+E) and immunized Ldlr$^{-/-}$ mice after (B+C) chow and (D+E) 3 weeks of feeding on the HFC diet, respectively. * Significantly different from non-immunized mice on chow diet. (*,  and *: $p<0.05$; 0.01; 0.001 respectively).

Figure 13:
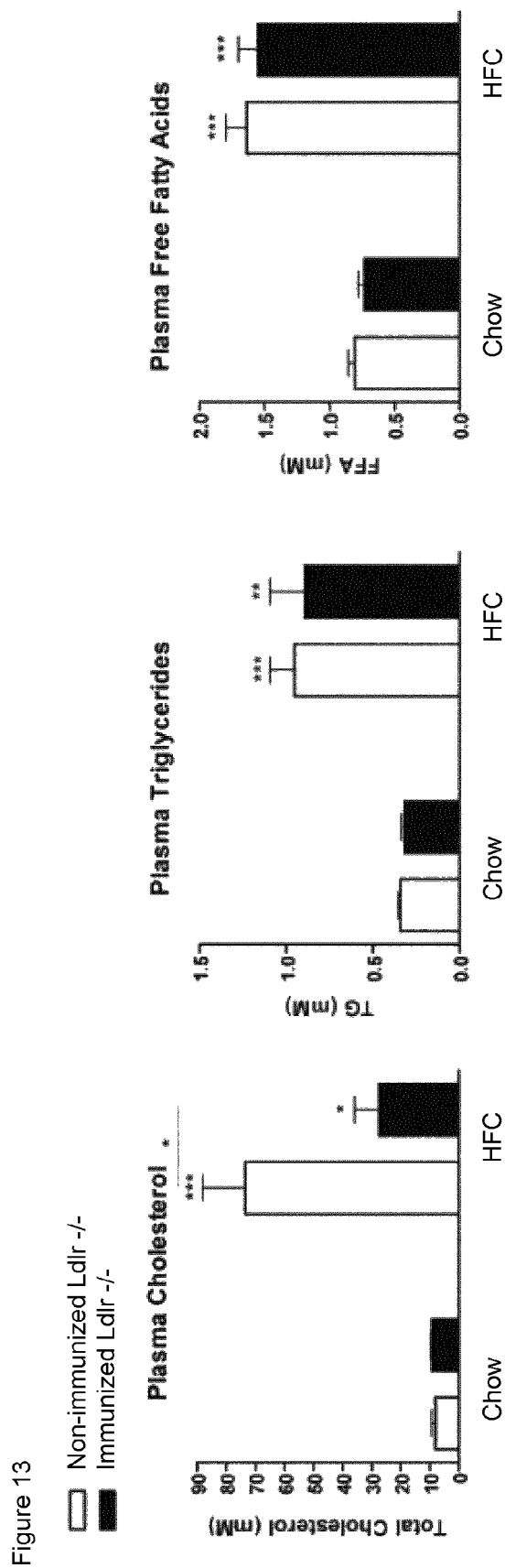

FIG. 13: Plasma lipid levels. Plasma cholesterol, triglycerides and free fatty acids after chow and 3 weeks of HFC diet in non-immunized and immunized Ldlr$^{-/-}$ mice. * Significantly different from non-immunized mice on chow diet. (*,  and *: $p<0.05$; 0.01; 0.001 respectively)

FIG. 14: Parameters of hepatic inflammation. (A) Liver sections were stained for infiltrated macrophages and neutrophils (Mac-1), neutrophils (NIMP) and T cells (CD3), respectively, and counted. (B–E) Representative pictures of Mac-1 staining (200×) after feeding on the chow (B+C) and HFC diet (D+E) in non-immunized (B+D) and immunized (C+E) Ldlr$^{-/-}$ mice, respectively. (F) Gene expression analysis for tumour necrosis factor (Tnf), interleukin 6 (Il6) and 1β (Il1β) and monocyte chemoattractant protein 1 (Mcp1). * Significantly different from non-immunized mice on chow diet. *,  and * indicate $p<0.05$, 0.01 and 0.001 respectively.

Figure 15:
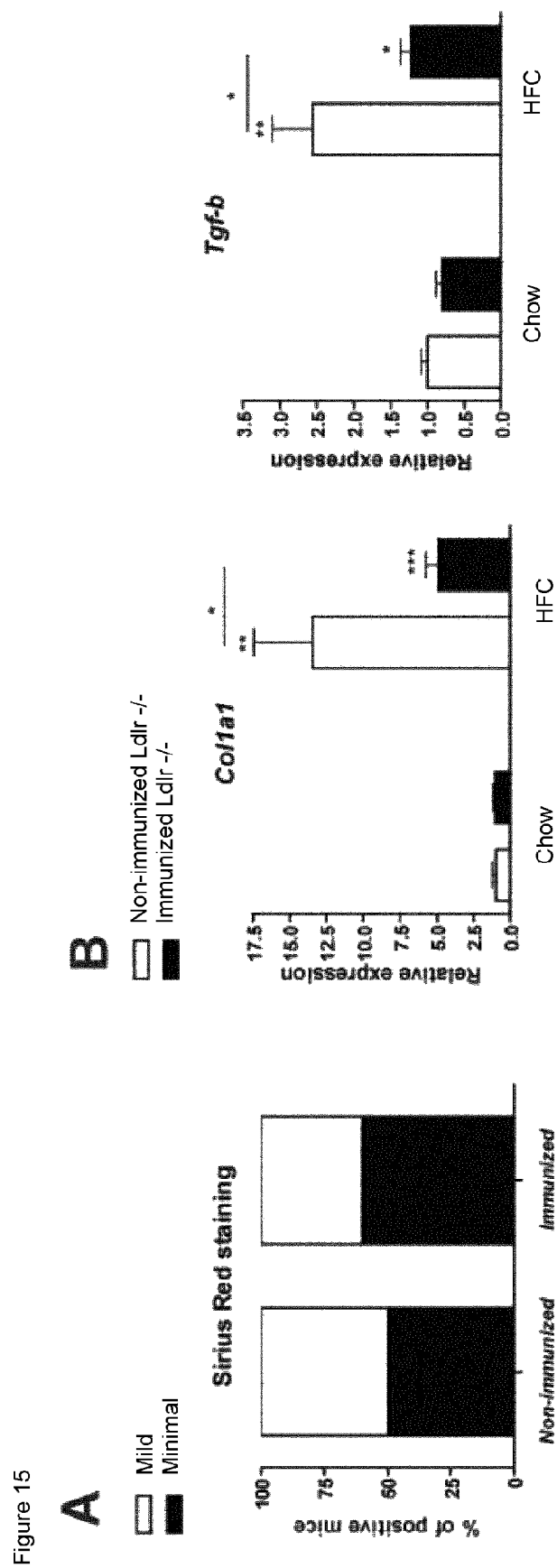

FIG. 15: Parameters of hepatic fibrosis. (A) Quantification of sirius red (collagen) after 3 weeks of HFC diet. Livers were quantified as minimal, mild or moderate positive for collagen around and in between the blood vessels of the liver. (B) Gene expression analysis of the fibrosis markers, collagen (Col1a1) and transforming growth factor beta (Tgf-β). * Significantly different from non-immunized mice on chow diet. *,  and * indicate $p<0.05$, 0.01 and 0.001 respectively.

FIG. 16: Foamy Kupffer cells. (A) Liver sections were stained for CD68 (Kupffer cells) and scored for the level of foamy appearance: 1 (mild foamy appearance) to 3 (severe foamy appearance). Mean scores were calculated from six microscopic views. (B) Gene expression analysis of the Kupffer cell activation marker, CD68. (C) Representative images of liver sections stained for CD68 for the Ldlr$^{-/-}$ mice on a chow diet without and with immunization and for the Ldlr$^{-/-}$ mice on the HFC diet without and with immunization respectively at a 200× magnification. (D) Electron microscopy of foamy Kupffer cells. Acid phosphatase staining indicating the lysosomes of the Kupffer cells in non-immunized and immunized Ldlr$^{-/-}$ mice on the HFC diet.* Significantly different from non-immunized mice on chow diet. * and *** indicate $p<0.05$ and 0.001 respectively.

Figure 17:
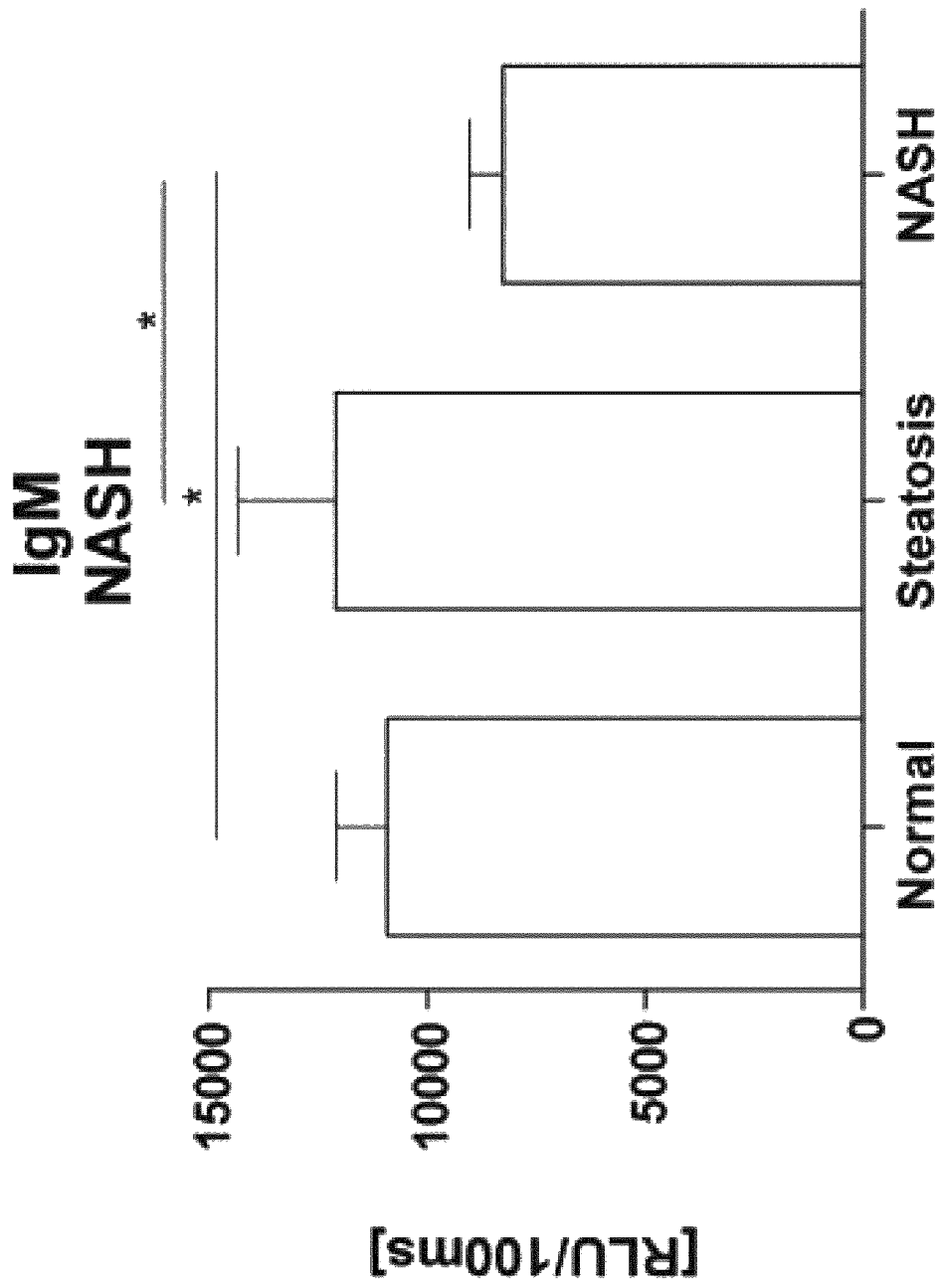

FIG. 17: IgM autoantibodies in human NASH patients. Plasma IgM autoantibodies to oxLDL (CuOx) in obese subjects with or without fatty liver disease were measured at a dilution of 1:100 (n=66). * Significantly different from subjects with a healthy liver (* indicates $p<0.05$).

Figure 18:
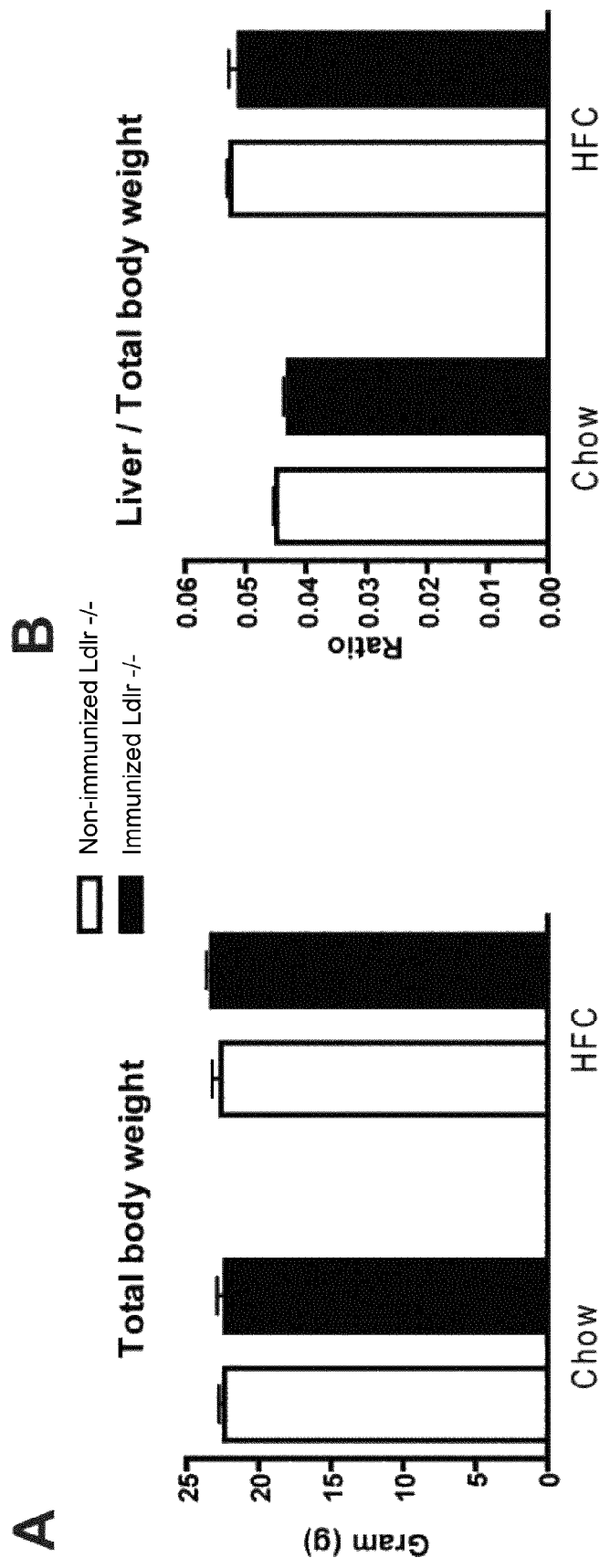

FIG. 18: Weight. (A) Total body weight and (B) ratio of liver weight to total body weight in in non-immunized and immunized Ldlr$^{-/-}$ mice on the HFC diet.

Figure 19:
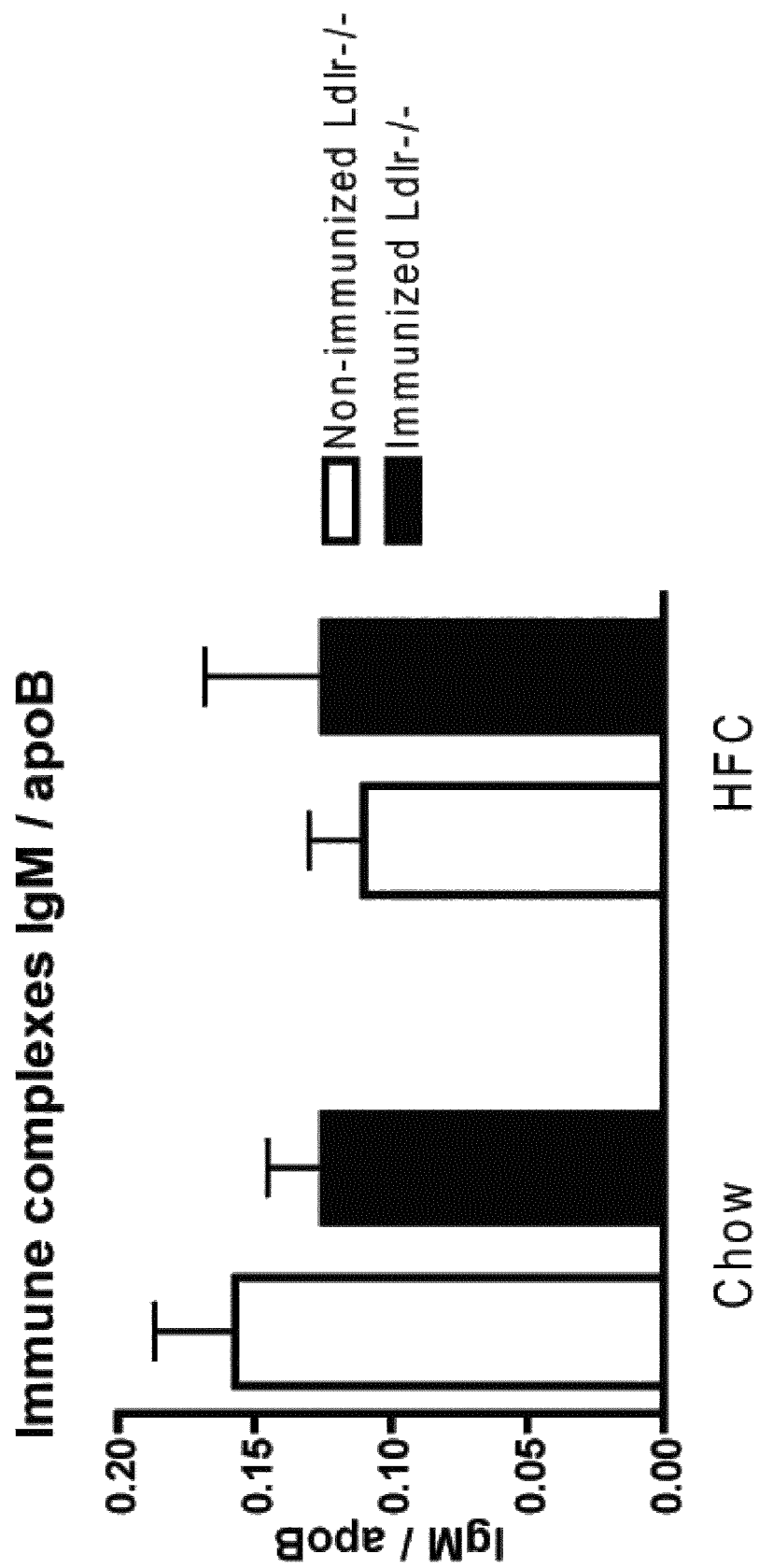

FIG. 19: Circulating immune complexes in plasma. The ratio of IgM/apoB immune complexes in non-immunized and immunized Ldlr$^{-/-}$ mice on chow and HFC diet.

Figure 20:
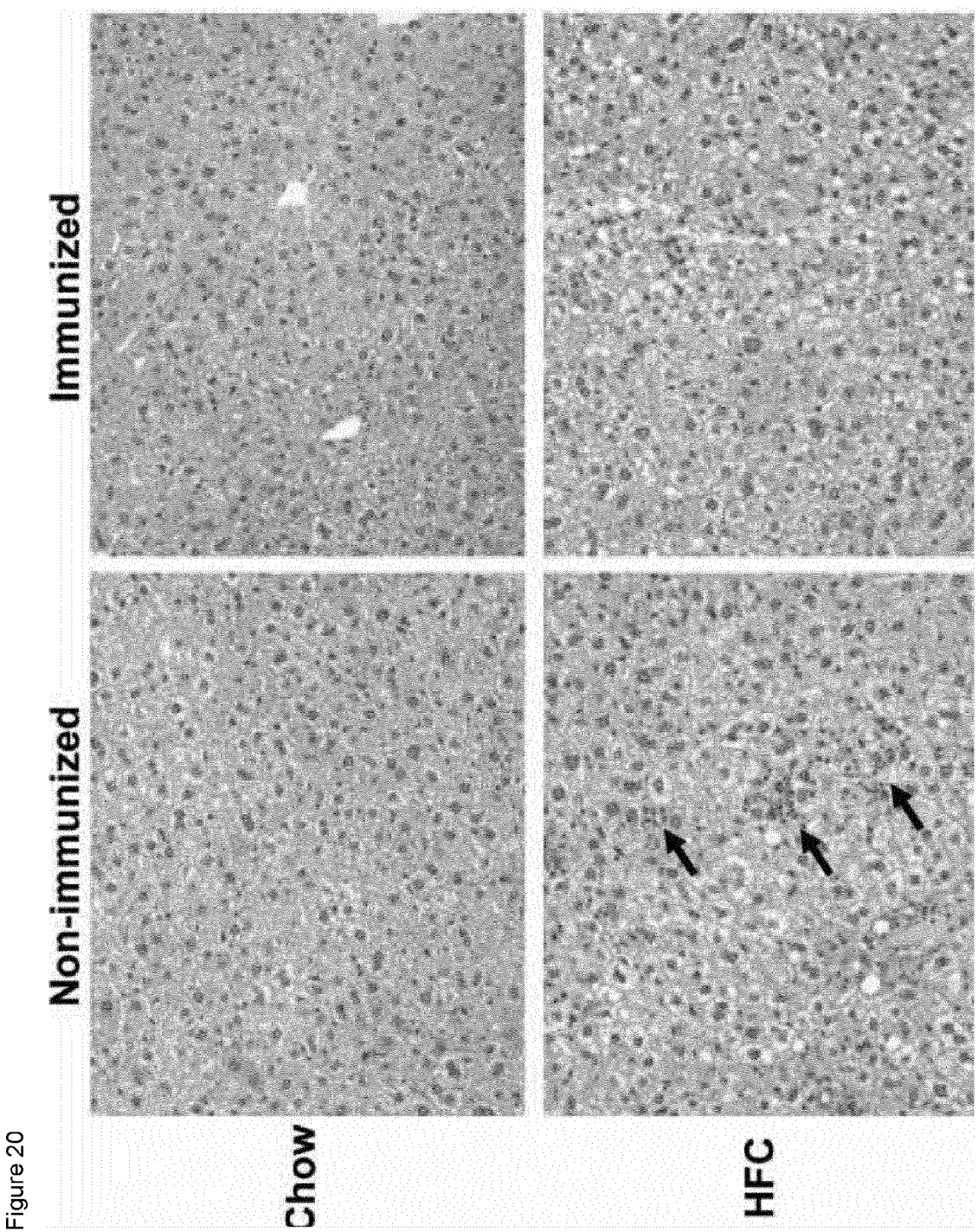

FIG. 20: General liver histology. Representative pictures (200× magnification) of Hematoxylin Eosin (HE) staining after chow and 3 weeks of HFC diet in non-immunized and immunized Ldlr$^{-/-}$ mice.

Figure 21:
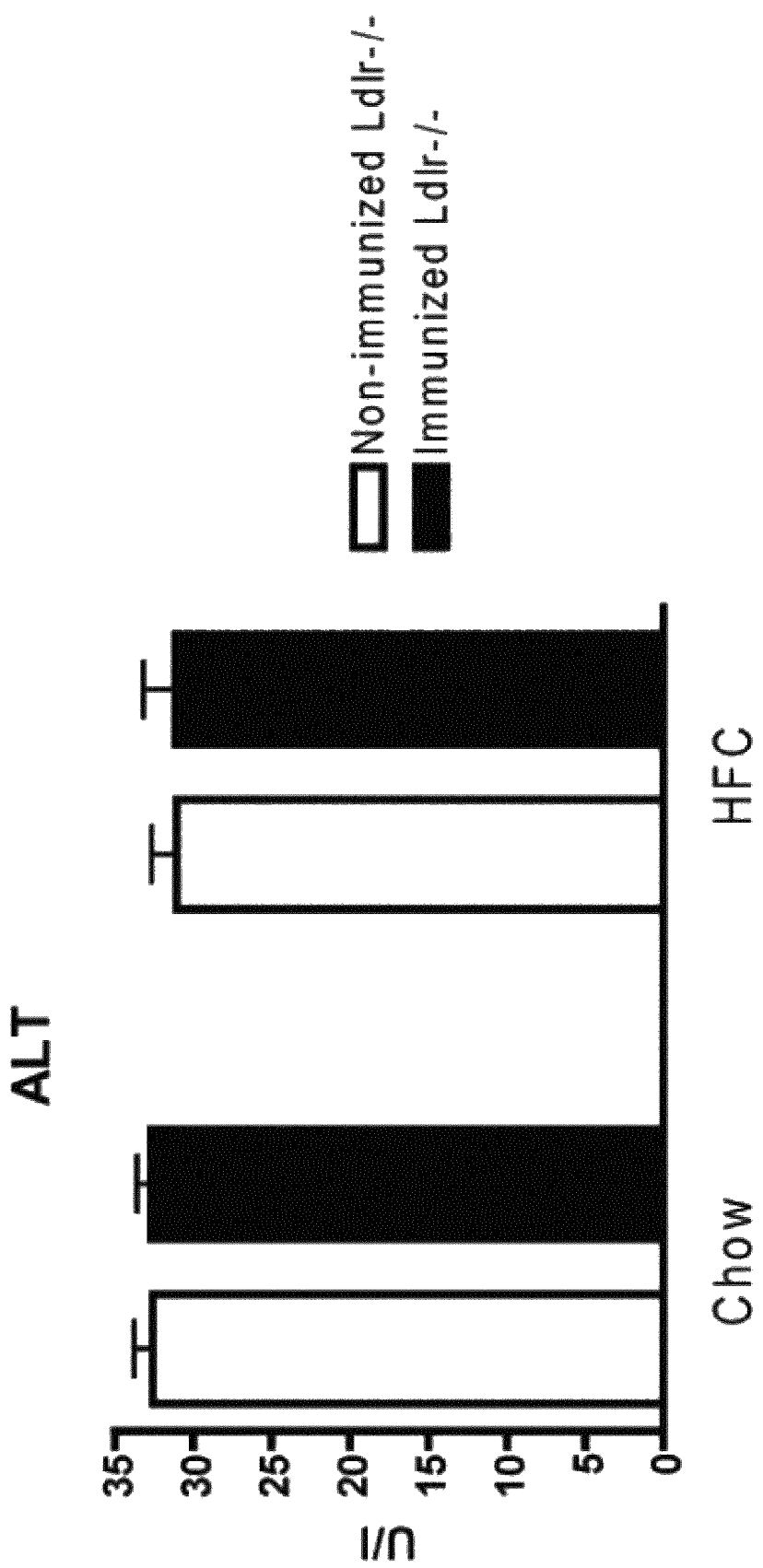

FIG. 21: Plasma ALT levels. Aminotransferase (ALT) levels in plasma of non-immunized and immunized Ldlr$^{-/-}$ mice after chow and HFC feeding.

EXAMPLES

Example 1

Experimental Procedures

Preparation of Immunogen

For immunization, the heat-inactivated R36A strain of Streptococcus pneumoniae (Birmingham, Ala.) was used, still bearing the PC headgroup epitope similar to oxLDL. Colonies of the R36A strain were harvested at mid log phase after incubation at 37° C. on blood agar plates and transferred to Todd-Hewitt plus 0.5% yeast broth. The mid log phase is characterized by an OD value of 0.425 to 0.45 at 600 nm. *S. pneumoniae* was heat-inactivated at 60° C. for 30 min, after which no colonies of this suspension were detected on blood agar plates. For freezer stocks, small aliquots of *S. pneumoniae* at mid log density were harvested and suspended in Todd-Hewitt plus 80% sterile glycerol and stored at −80° C. (67).

Subjects

Sixty-six severely obese patients undergoing bariatric surgery at the Maastricht University Medical Centre were included in the study. None of the subjects suffered from autoimmune diseases, viral hepatitis, or reported excessive alcohol intake (>20 g/day). The study was approved by the local Ethics Committee and conducted in line with the 1975 Declaration of Helsinki guidelines and the Seoul 2008 amendments. All subjects gave written informed consent. Liver wedge biopsies were obtained during surgery as previously described (68). Biopsies were evaluated for histological features (Brunt's criteria) by an experienced pathologist who was blinded to the clinical context of the biopsy and laboratory parameters.

Mice, Immunization and Diet

LDLr−/− mice on a C57/BL6 background were housed under standard conditions and had access to food and water ad libitum. Experiments were performed according to Dutch laws, approved by the Animal Experiment Committee of Maastricht University. The immunization protocol started in 12-week-old female mice, fed a normal chow diet. Mice were divided into four groups (n=10 for each group) and received $10^8$ CFU of pneumococcal immunogen emulsified in 200 µl sterile 0.9% NaCl for the primary subcutaneous immunization, after which three intraperitoneal booster immunizations were administered at two-week intervals. The control group received a NaCl injection only. After immunization, the mice were given normal chow, forming the control group, or a high fat cholesterol diet (HFC diet), forming the experimental group, for 3 weeks. Blood from the tail vein was collected after the dietary period and mice were then sacrificed by cervical dislocation. Liver tissue was isolated and snap-frozen in liquid nitrogen and stored at −80° C. or fixed in 4% formaldehyde/PBS.

Electron Microscopy

A detailed overview about the (post)fixation, embedding, cutting and type of electron microscope was described previously (16). To stain the Kupffer cell lysosomes, acid phosphatase (ACPase) enzyme cytochemistry was performed. Small wedge biopsies of the liver were perfused by syringe injection with icecold 2% purified glutaraldehyde in 0.1M cacodylater buffer (pH 7.4) for 15 min. The wedge biopsies were cut in small pieces and kept in 0.1M cacodylate buffer+ 7.5% sucrose at 4° C. until further processing; the buffer solution was refreshed weekly. The samples were frozen for 1 h at −30° C. whereafter 50 micrometer thick cryosections were made. These sections were incubated according to the cerium-based method of Robinson and Karnovsky for the localization of ACPase (82). After the incubation, the sections were washed two times in 0.1M cacodylate buffer supplemented with 5% sucrose, refixed in 3% glutaraldehyde in cacodylate buffer for 1 h and rinsed overnight in veronal acetate buffer (pH 7.4, 4° C.). The sections were then post-fixed for 30 min in 2% osmium tetroxide in veronal buffer+ 4% sucrose and then routinely processed for embedding in epon.

Gene Expression Analysis

Total RNA was isolated from mouse liver tissues by homogenizing frozen liver tissues together with 1.0 ml Tri Reagent (Sigma Aldrich, Saint Louis, USA) and 1.0 mm of glass beads in a closed tube for 30 s at 4800 rpm. After centrifugation with the addition of 200 µl chloroform, an aqueous phase was visible and was transferred to a fresh tube. Isopropanol (0.5 ml) was added and upon another centrifugation step, RNA was precipitated. The RNA pellet was washed by adding 1.0 ml 70% ethanol. After centrifugation, the supernatant was removed and the pellet was dissolved in an appropriate volume of DEPC sterile H2O. All the materials used were RNAse free and the samples were placed on ice during the procedure. Afterwards the RNA concentration and RNA quality were determined on a NanoDrop ND-1000 spectrophotometer.

Total RNA (500 ng) from each individual mouse was converted into first strand complementary DNA (cDNA) with an iScript cDNA synthesis kit (Bio-Rad, Hercules, USA). Subsequently, changes in the gene expression of inflammatory markers were determined by quantitative PCR (qPCR) on a Biorad MyIQ with IQ5 v2.1 software using IQ SensiMix™ SYBR with Fluorescein (Quantace, London, UK) or on an Applied Biosystems 7900HT with SensiMix™ SYBR (Quantace, London, UK), which is capable of screening more samples during one single run, and 10 ng of cDNA. For each gene, a standard curve was generated with a serial dilution of a liver cDNA pool with a known concentration. To standardize for the amount of cDNA, Cyclophillin A was used as the reference gene. Primer sets for the selected gene were developed with Primer Express v2.0 (Applied Biosystems, Foster City, USA) using default settings. Data from qPCR were analysed according to the comparative Ct quantities.

Liver Histology

Frozen liver sections (7 µm) were fixed with acetone and blocked against endogenous peroxidase by incubation with 0.25% of 30% H2O2 for 5 minutes. Primary antibodies were used against infiltrated macrophages (macrophage marker, Mac-1), CD68 Kupffer cells (CD68 marker, FA11), T cells (T cell marker, KT3), fibroblasts (fibroblast marker, ERTR7) and neutrophils (neutrophil marker, NIMP). For NIMP staining no amplification step was needed as a secondary antibody, α-rat-PO, was used. Prior to incubation with the first antibody, slides were incubated with 4% fetal calf serum (FCS), 1×PBS plus an amplification step: 1:5 Avidin D Block solution (ABC kit, Vector Laboratories, USA). Primary antibodies were dissolved in 4% FCS, 1×PBS+1st antibody (1:1000 for Mac1, 1:200 for NIMP, 1:100 for CD68 and 1:5 for CD3) plus an amplification step: 1:5 Biotin Block solution (ABC kit, Vector Laboratories, USA). Incubation with the 2nd antibody 1:300 for α-rat-BIO (1:100 for α-rat-PO) was carried out in 4% FCS, 2% normal mouse serum (NMS) and 1×PBS. Afterwards the slides were washed and incubated for an additional amplification step in 1×PBS+1:50 Avidin D solution+ 1:50 Biotin solution (ABC kit, Vector Laboratories, USA). Then, 13-amino-9-ethylcarbazole (AEC) was applied as the colour substrate using an AEC kit (2% buffer, 3% AEC, 2% H2O2 in demi water) and haematoxylin for nuclear counter-staining. Sections were enclosed with Faramount aqueous mounting medium.

Paraffin-embedded liver sections (4 µm) were stained with Haematoxylin-Eosin (Haematoxylin, Klinipath, Duiven, The Netherlands and Eosin, Sigma-Aldrich, Saint Louis, USA) after deparaffination in xylol and dehydrated with 90%, 70% and 50% ethanol respectively. Sections were mounted with Entallan.

For electron microscopy, liver sections were first perfused with glutaraldehyde. When perfusion was complete, tissue was stored in glutaraldehyde fixative. Then, liver sections were washed in cacodylate buffer to remove the glutaraldehyde fixative followed by post-fixation in 1% osmium tetroxide for 1 hour. After this fixation, the osmium fixative was washed off using buffer before the liver sections were placed in alcohol (70%-100%). Further steps in the preparative procedure were then followed.

Statistical Analysis

The data were statistically analysed by performing two-tailed non-paired t-tests using GraphPad Prism, version 4.03 for Windows. Data were expressed as the mean±SEM and considered significant at p<0.05. *,  and * indicate p<0.05, 0.01 and 0.001 respectively.

Example 2

Increased IgM Antibody Titers Against Modified LDL after Immunization with Heat-Inactivated Pneumococci To determine whether IgM autoantibodies to oxLDL have a protective effect on liver inflammation, mice were immunized for 9 weeks with heat-inactivated pneumococci, known to induce high anti-oxLDL IgM titers dominated by T15-idiotypic IgM. To induce NASH, the mice received a HFC diet during the last 3 weeks. Total body weight and the ratio of liver weight to total body weight were not significantly different between the different groups (FIG. 18). Immunization of Ldlr−/− mice with heat-inactivated pneumococci resulted in a strong increase in IgM titers to oxLDL (FIG. 11A+B). Only weak, although significant IgG responses were observed. We found an IgM dominated thymus-independent type-2 response highly specific for PC (FIG. 11C+D). The levels of circulating IgM/apoB immune complexes did not differ between the groups, likely indicating efficient clearance of oxLDL (FIG. 19).

Example 3

Figure 12A:
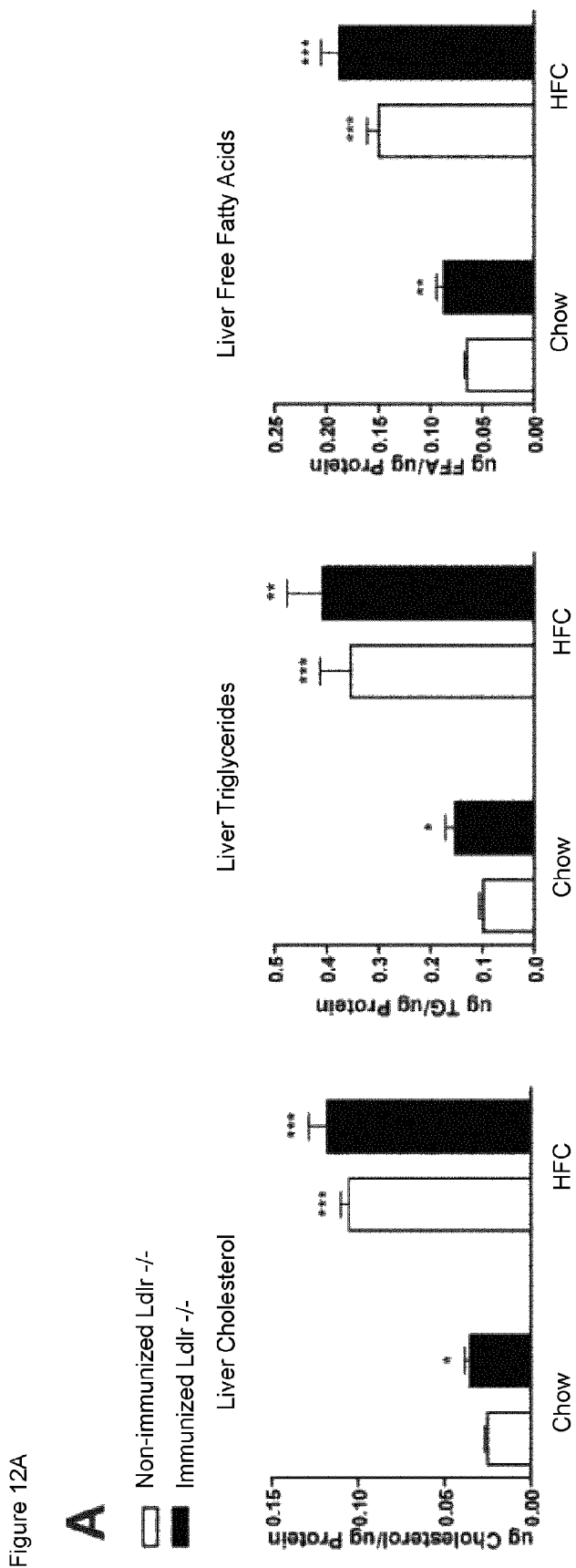

No Difference in Liver Lipid Levels Between Immunized and Non-Immunized Ldlr−/− Mice after 3 Weeks of HFC Diet To investigate liver lipid levels in hyperlipidemic mice with or without immunization, biochemical assessment of liver cholesterol, triglycerides (TG) and free fatty acids (FFA) was carried out (FIG. 12A). After 3 weeks on HFC diet, a clear increase in all liver lipid levels was observed compared to mice on a chow diet. Liver lipid levels did not differ between immunized and non-immunized Ldlr−/− mice on the HFC diet. Mice on the chow diet showed a small increase in liver lipid levels after immunization when compared to non-immunized Ldlr−/− mice. Oil red O staining confirmed the biochemical liver lipid measurements (FIG. 2B-E and FIG. 20).

Example 4

Decreased Plasma Cholesterol in Immunized Ldlr−/− Mice on the HFC Diet Compared to Control Mice The effect of immunization on plasma lipids was assessed by measuring the levels of plasma cholesterol, TG and FFA. After feeding on the HFC diet, a significant increase was observed for all plasma lipids compared to mice on a chow diet. Interestingly, plasma cholesterol was reduced in immunized Ldlr−/− mice compared to non-immunized mice on the HFC diet. Plasma TG and FFA did not differ between the groups following the HFC diet. On chow diet, plasma lipid levels did not differ between the groups (FIG. 13).

Example 5

Figure 14A:
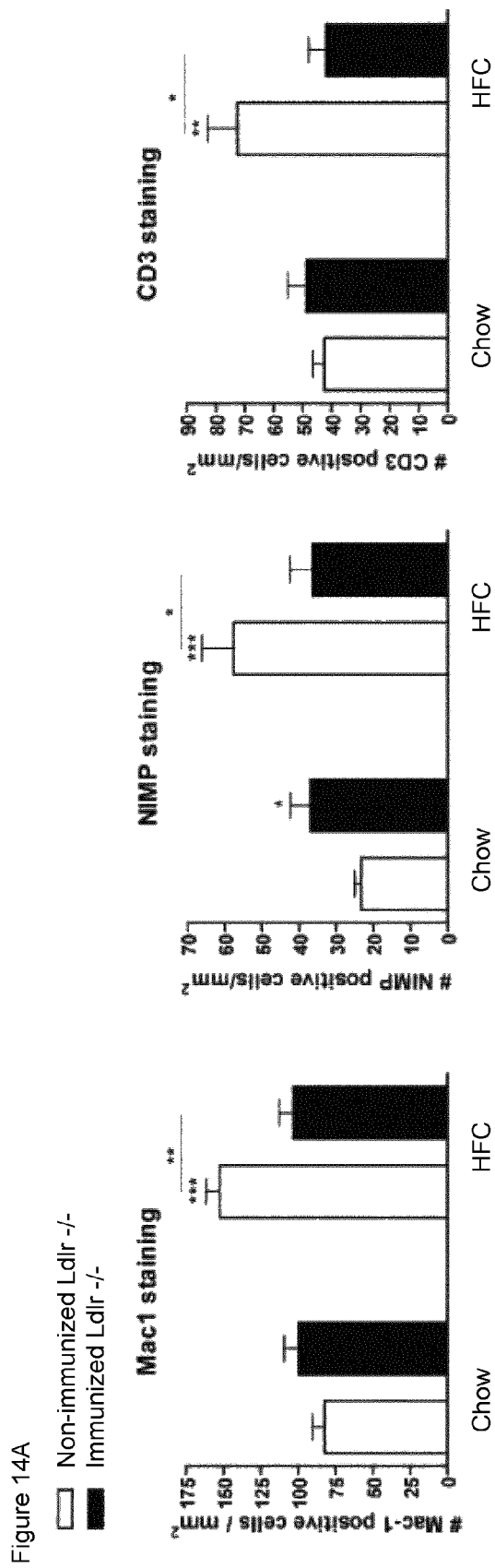
Figure 14F:
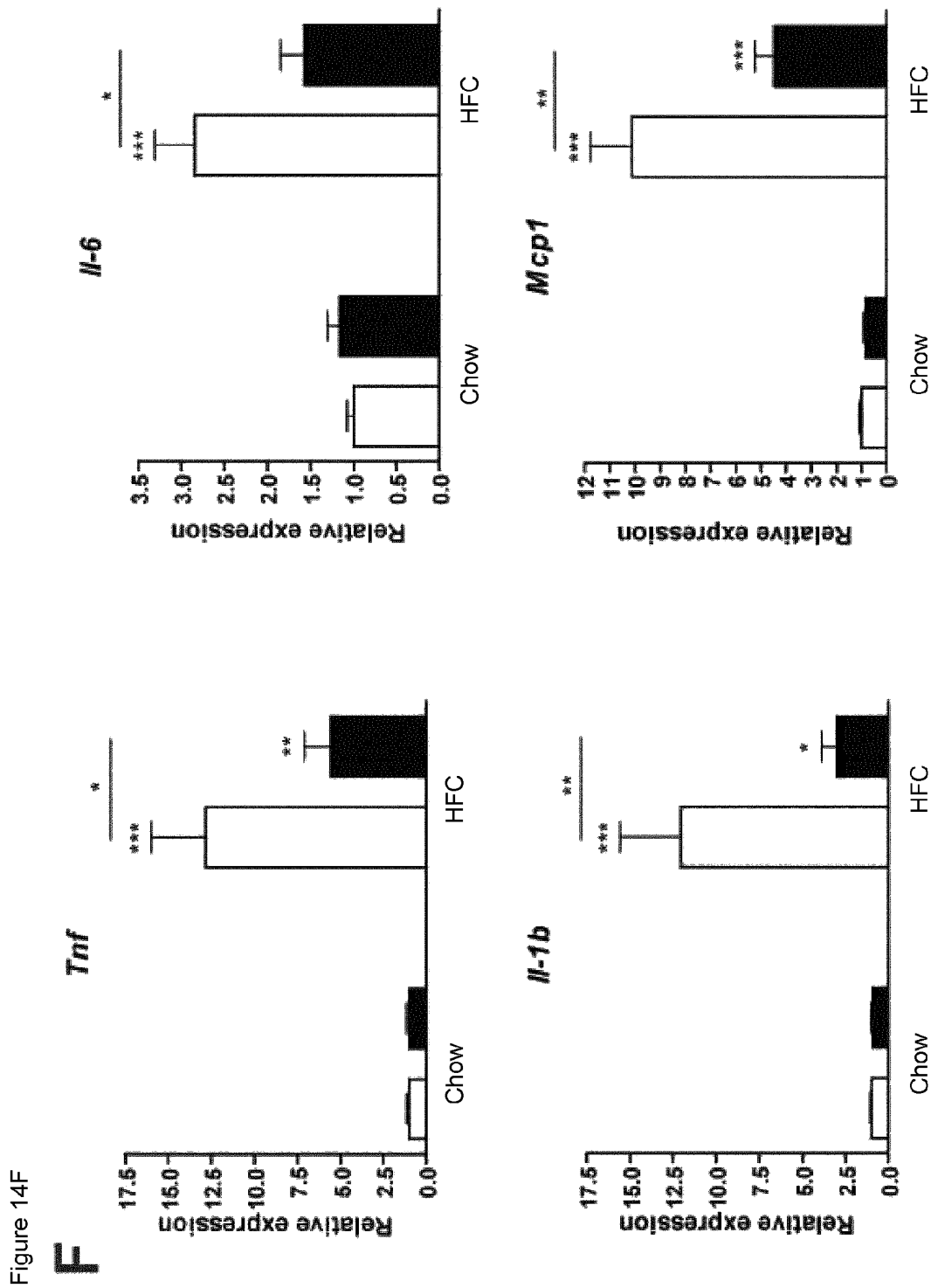

Decreased Hepatic Inflammation in Ldlr−/− Mice Immunized with Heat-Inactivated Pneumococci To determine whether immunization of Ldlr−/− mice with heat-inactivated pneumococci affects hepatic inflammation, liver sections were stained for the inflammatory cell markers Mac-1 (infiltrated macrophages and neutrophils), NIMP (neutrophils) and CD3 (T cells). As shown in FIG. 14A, the number of infiltrated macrophages, neutrophils and T cells was lower in immunized Ldlr−/− mice compared to non-immunized mice after feeding the HFC diet. Moreover, the normal chow diet induced a significant increase in the number of neutrophils in immunized chow-fed mice compared to non-immunized mice. Representative histological pictures of the Mac-1 staining for all four experimental groups are shown in FIG. 14B-E. Further confirming the reduced hepatic inflammation in immunized Ldlr−/− mice on the HFC diet, gene expression analysis showed a significant decrease in the inflammatory markers tumour necrosis factor (Tnf), interleukin-1beta (Il-1b), interleukin 6 (Il-6) and monocyte chemoattractant protein-1 (Mcp1) in livers of immunized Ldlr−/− mice on the HFC diet compared to non-immunized mice (FIG. 14F). However, hepatic inflammation in Ldlr−/− mice on the HFC diet after immunization was still higher than chow-fed immunized mice according to the inflammatory markers Tnf, Il-1b and Mcp1. The presence of elevated transaminases in plasma like alanine aminotransferase (ALT) did not differ between the different groups (FIG. 21).

Example 6

After 3 Weeks of HFC Diet, Immunization Prevented Expression of Fibrosis-Related Genes in Ldlr−/− Mice Fibrosis is considered to be an advanced stage of NASH. Collagen staining (Sirius Red) was performed to determine the degree of fibrosis. No differences were observed between the experimental groups after 3 weeks of HFC diet (FIG. 15A), which is probably related to the short duration of the HFC diet. However, gene expression analysis for collagen type 1A1 (Col1A1) and transforming growth factor beta (Tgf-β) demonstrated that the mRNA levels of these fibrogenic genes were lower in immunized mice compared to non-immunized mice on the HFC diet (FIG. 15B).

Example 7

Figure 16D:
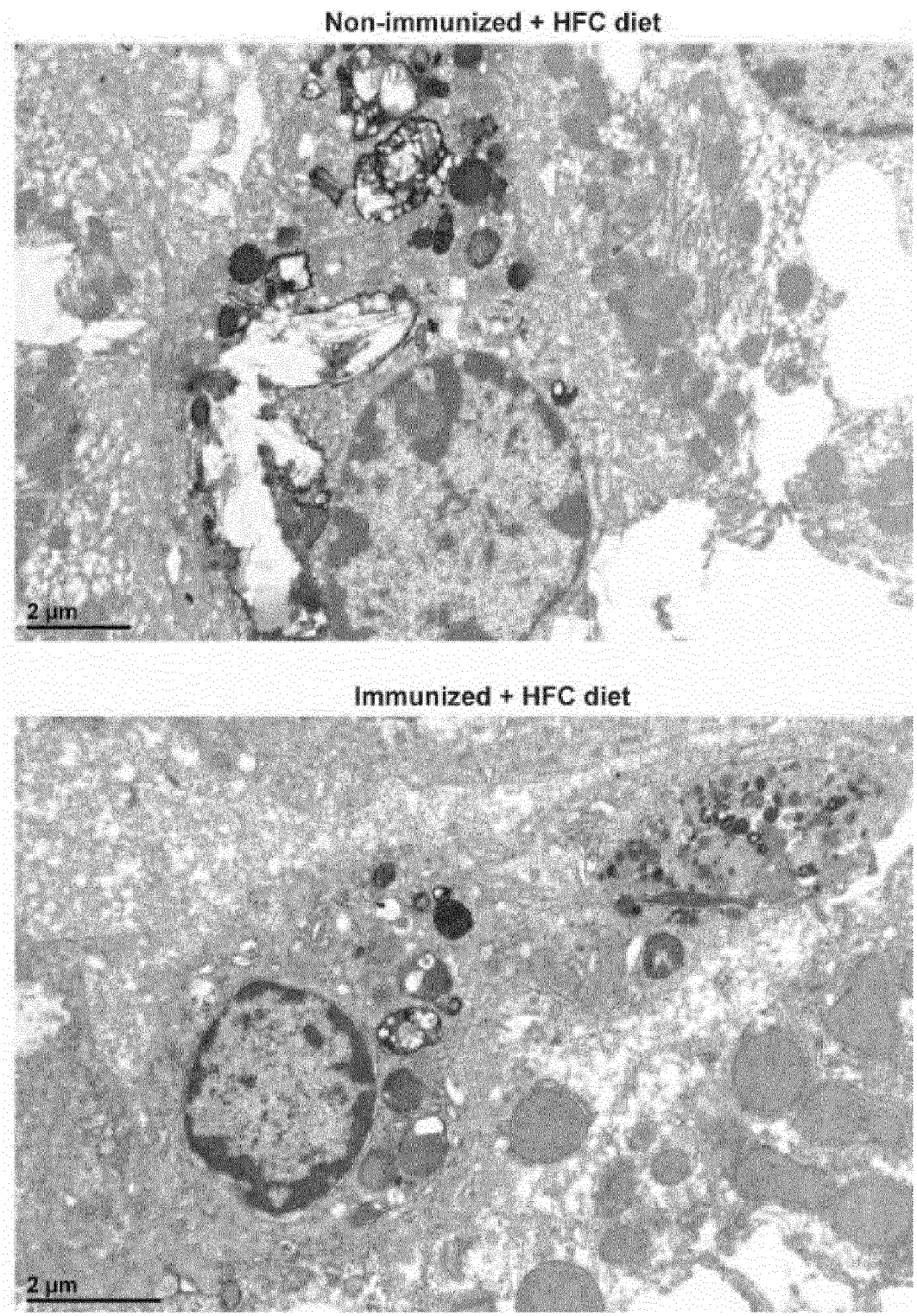

Decreased Foamy Appearance of Kupffer Cells in Immunized Ldlr−/− Mice on the HFC Diet Immunohistochemistry for CD68 was performed to characterize the KCs. Scoring of the CD68 positive sections revealed a reduction in size of foamy KCs in immunized Ldlr−/− mice compared to non-immunized mice on the HFC diet (FIG. 16A+C). Gene expression of Cd68 was reduced in the immunized Ldlr−/− mice compared to non-immunized mice on the HFC diet (FIG. 16B). Electron microscopy of KCs confirmed the differences in size of the KCs between immunized and non-immunized Ldlr−/− mice, and showed that the immunized mice upon HFC diet had less lysosomal cholesterol accumulation and cholesterol crystals compared to non-immunized mice (FIG. 16D).

Example 8

Decreased IgM Antibody Titers to oxLDL in NASH Patients

In order to investigate whether NASH patients have reduced levels of protective autoantibodies towards oxLDL, IgM levels were determined in plasma of patients with fatty liver disease. In NASH patients, plasma IgM levels against oxLDL were lower compared to subjects with a healthy liver or steatosis alone (FIG. 17). Plasma IgG levels against oxLDL were not different between groups (data not shown). These data suggest that NASH patients are more sensitive to oxLDL induced liver damage compared to subjects with a healthy liver or steatosis alone.

REFERENCES AND LITERATURE INCORPORATED BY REFERENCE

1. McCullough A J. The clinical features, diagnosis and natural history of nonalcoholic fatty liver disease. Clin Liver Dis 2004; 8:521-33, viii.
2. Clark J M, Diehl A M. Defining nonalcoholic fatty liver disease: implications for epidemiologic studies. Gastroenterology 2003; 124:248-50.
3. Parekh S, Anania F A. Abnormal lipid and glucose metabolism in obesity: implications for nonalcoholic fatty liver disease. Gastroenterology 2007; 132:2191-207.
4. Mari M, Caballero F, Colell A, Morales A, Caballeria J, Fernandez A, Enrich C, Fernandez-Checa J C, Garcia-Ruiz C. Mitochondrial free cholesterol loading sensitizes to TNF- and Fas-mediated steatohepatitis. Cell Metab 2006; 4:185-98.
5. Wouters K, van Gorp P J, Bieghs V, Gijbels M J, Duimel H, Lutjohann D, Kerksiek A, van Kruchten R, Maeda N, Staels B, van Bilsen M, Shiri-Sverdlov R, Hofker M H. Dietary cholesterol, rather than liver steatosis, leads to hepatic inflammation in hyperlipidemic mouse models of nonalcoholic steatohepatitis. Hepatology 2008; 48:474-86.
6. Tous M, Ferre N, Rull A, Marsillach J, Coll B, Alonso-Villayerde C, Camps J, Joven J. Dietary cholesterol and differential monocyte chemoattractant protein-1 gene expression in aorta and liver of apo E-deficient mice. Biochem Biophys Res Commun 2006; 340:1078-84.
7. Kainuma M, Fujimoto M, Sekiya N, Tsuneyama K, Cheng C, Takano Y, Terasawa K, Shimada Y. Cholesterol-fed rabbit as a unique model of nonalcoholic, nonobese, non-insulin-resistant fatty liver disease with characteristic fibrosis. J Gastroenterol 2006; 41:971-80.
8. Tannock L R, O'Brien K D, Knopp R H, Retzlaff B, Fish B, Wener M H, Kahn S E, Chait A. Cholesterol feeding increases C-reactive protein and serum amyloid A levels in lean insulin-sensitive subjects. Circulation 2005; 111:3058-62.
9. Hansson G K, Robertson A K, Soderberg-Naucler C. Inflammation and atherosclerosis. Annu Rev Pathol 2006; 1:297-329.
10. Bieghs V, Wouters K, Van Gorp P J, Gijbels M J, De Winther M P, Binder C J, Lutjohann D, Febbraio M, Moore K J, Van Bilsen M, Hofker M H, Shiri-Sverdlov R. Role of Scavenger Receptor A and CD36 in Diet-induced Nonalcoholic Steatohepatitis in Hyperlipidemic Mice. Gastroenterology.
11. Yamada Y, Doi T, Hamakubo T, Kodama T. Scavenger receptor family proteins: roles for atherosclerosis, host defence and disorders of the central nervous system. Cell Mol Life Sci 1998; 54:628-40.
12. Karvonen J, Paivansalo M, Kesaniemi Y A, Horkko S. Immunoglobulin M type of autoantibodies to oxidized low-density lipoprotein has an inverse relation to carotid artery atherosclerosis. Circulation 2003; 108:2107-12.
13. Horkko S, Bird D A, Miller E, Itabe H, Leitinger N, Subbanagounder G, Berliner J A, Friedman P, Dennis E A, Curtiss L K, Palinski W, Witztum J L. Monoclonal autoantibodies specific for oxidized phospholipids or oxidized phospholipid-protein adducts inhibit macrophage uptake of oxidized low-density lipoproteins. J Clin Invest 1999; 103:117-28.
14. Binder C J, Silverman G J. Natural antibodies and the autoimmunity of atherosclerosis. Springer Semin Immunopathol 2005; 26:385-404.
15. Shaw P X, Horkko S, Chang M K, Curtiss L K, Palinski W, Silverman G J, Witztum J L. Natural antibodies with the T15 idiotype may act in atherosclerosis, apoptotic clearance, and protective immunity. J Clin Invest 2000; 105: 1731-40.
16. Palinski W, Horkko S, Miller E, Steinbrecher U P, Powell H C, Curtiss L K, Witztum J L. Cloning of monoclonal autoantibodies to epitopes of oxidized lipoproteins from apolipoprotein E deficient mice. Demonstration of epitopes of oxidized low density lipoprotein in human plasma. J Clin Invest 1996; 98:800-14.
17. Binder C J, Horkko S, Dewan A, Chang M K, Kieu E P, Goodyear C S, Shaw P X, Palinski W, Witztum J L, Silverman G J. Pneumococcal vaccination decreases atherosclerotic lesion formation: molecular mimicry between *Streptococcus pneumoniae* and oxidized LDL. Nat Med 2003; 9:736-43.
18. Itabe H, Suzuki K, Tsukamoto Y, Komatsu R, Ueda M, Mori M, Higashi Y, Takano T. Lysosomal accumulation of oxidized phosphatidylcholine-apolipoprotein B complex in macrophages: intracellular fate of oxidized low density lipoprotein. Biochim Biophys Acta 2000; 1487:233-45.
19. Ehara S, Ueda M, Naruko T, Haze K, Itoh A, Otsuka M, Komatsu R, Matsuo T, Itabe H, Takano T, Tsukamoto Y, Yoshiyama M, Takeuchi K, Yoshikawa J, Becker A E. Elevated levels of oxidized low density lipoprotein show a positive relationship with the severity of acute coronary syndromes. Circulation 2001; 103:1955-60.
20. Bieghs V, Wouters K, van Gorp P J, Gijbels M J, de Winther M P, Binder C J, Lutjohann D, Febbraio M, Moore K J, van Bilsen M, Hofker M H, Shiri-Sverdlov R. Role of scavenger receptor A and CD36 in diet-induced nonalcoholic steatohepatitis in hyperlipidemic mice. Gastroenterology; 138:2477-86, 2486 e1-3.
21. Platt N, Suzuki H, Kurihara Y, Kodama T, Gordon S. Role for the class A macrophage scavenger receptor in the phagocytosis of apoptotic thymocytes in vitro. Proc Natl Acad Sci USA 1996; 93:12456-60.
22. Febbraio M, Hajjar D P, Silverstein R L. CD36: a class B scavenger receptor involved in angiogenesis, atherosclerosis, inflammation, and lipid metabolism. J Clin Invest 2001; 108:785-91.
23. Cotena A, Gordon S, Platt N. The class A macrophage scavenger receptor attenuates CXC chemokine production and the early infiltration of neutrophils in sterile peritonitis. J Immunol 2004; 173:6427-32.
24. Kayo S, Ohsawa M, Ehara S, Naruko T, Ikura Y, Hai E, Yoshimi N, Shirai N, Tsukamoto Y, Itabe H, Higuchi K, Arakawa T, Ueda M. Oxidized low-density lipoprotein levels circulating in plasma and deposited in the tissues: comparison between Helicobacter pylori-associated gastritis and acute myocardial infarction. Am Heart J 2004; 148:818-25.

25. Caligiuri G, Khallou-Laschet J, Vandaele M, Gaston A T, Delignat S, Mandet C, Kohler H V, Kaveri S V, Nicoletti A. Phosphorylcholine-targeting immunization reduces atherosclerosis. J Am Coll Cardiol 2007; 50:540-6.

26. Binder C J, Chang M K, Shaw P X, Miller Y I, Hartvigsen K, Dewan A, Witztum J L. Innate and acquired immunity in atherogenesis. Nat Med 2002; 8:1218-26.

27. Chang M K, Bergmark C, Laurila A, Horkko S, Han K H, Friedman P, Dennis E A, Witztum J L. Monoclonal antibodies against oxidized low-density lipoprotein bind to apoptotic cells and inhibit their phagocytosis by elicited macrophages: evidence that oxidation-specific epitopes mediate macrophage recognition. Proc Natl Acad Sci USA 1999; 96:6353-8.

28. Reardon C A, Miller E R, Blachowicz L, Lukens J, Binder C J, Witztum J L, Getz G S. Autoantibodies to OxLDL fail to alter the clearance of injected OxLDL in apolipoprotein E-deficient mice. J Lipid Res 2004; 45:1347-54.

29. Chalasani N, Deeg M A, Crabb D W. Systemic levels of lipid peroxidation and its metabolic and dietary correlates in patients with nonalcoholic steatohepatitis. Am J Gastroenterol 2004; 99:1497-502.

30. James O, Day C. Non-alcoholic steatohepatitis: another disease of affluence. Lancet 1999; 353:1634-6.

31. Ikura Y, Ohsawa M, Suekane T, Fukushima H, Itabe H, Jomura H, Nishiguchi S, Inoue T, Naruko T, Ehara S, Kawada N, Arakawa T, Ueda M. Localization of oxidized phosphatidylcholine in nonalcoholic fatty liver disease: impact on disease progression. Hepatology 2006; 43:506-14.

32. Sanyal A J, Campbell-Sargent C, Mirshahi F, Rizzo W B, Contos M J, Sterling R K, Luketic V A, Shiffman M L, Clore J N. Nonalcoholic steatohepatitis: association of insulin resistance and mitochondrial abnormalities. Gastroenterology 2001; 120:1183-92.

33. McClain C J, Mokshagundam S P, Barve S S, Song Z, Hill D B, Chen T, Deaciuc I. Mechanisms of non-alcoholic steatohepatitis. Alcohol 2004; 34:67-79.

34. Sanyal A J, Chalasani N, Kowdley K V, McCullough A, Diehl A M, Bass N M, Neuschwander-Tetri B A, Lavine J E, Tonascia J, Unalp A, Van Natta M, Clark J, Brunt E M, Kleiner D E, Hoofnagle J H, Robuck P R. Pioglitazone, vitamin E, or placebo for nonalcoholic steatohepatitis. N Engl J Med; 362:1675-85.

35. Gupte A A, Liu J Z, Ren Y, Minze L J, Wiles J R, Collins A R, Lyon C J, Pratico D, Finegold M J, Wong S T, Webb P, Baxter J D, Moore D D, Hsueh W A. Rosiglitazone attenuates age- and dietassociated nonalcoholic steatohepatitis in male low□density lipoprotein receptor knockout mice. Hepatology 2010; 52(6):2001-11.

36. Shiri-Sverdlov R, Wouters K, van Gorp P J, Gijbels M J, Noel B, Buffat L, Staels B, Maeda N, van Bilsen M, Hofker M H. Early diet-induced non-alcoholic steatohepatitis in APOE2 knock-in mice and its prevention by fibrates. J Hepatol 2006; 44:732-41.

37. Yamaguchi K, Yang L, McCall S, Huang J, Yu X X, Pandey S K, Bhanot S, Monia B P, Li Y X, Diehl A M. Inhibiting triglyceride synthesis improves hepatic steatosis but exacerbates liver damage and fibrosis in obese mice with nonalcoholic steatohepatitis. Hepatology 2007; 45:1366-74.

38. Matsuzawa N, Takamura T, Kurita S, Misu H, Ota T, Ando H, Yokoyama M, Honda M, Zen Y, Nakanuma Y, Miyamoto K, Kaneko S. Lipid-induced oxidative stress causes steatohepatitis in mice fed an atherogenic diet. Hepatology 2007; 46:1392-403.

39. Bieghs V, Wouters K, Van Gorp P J, Gijbels M J, De Winther M P, Binder C J, Lutjohann D, Febbraio M, Moore K J, Van Bilsen M, Hofker M H, Shiri-Sverdlov R. Role of Scavenger Receptor A and CD36 in Diet-induced Nonalcoholic Steatohepatitis in Hyperlipidemic Mice. Gastroenterology 2010.

40. Kang Q, Chen A. Curcumin eliminates oxidized LDL roles in activating hepatic stellate cells by suppressing gene expression of lectin-like oxidized LDL receptor-1. Lab Invest 2009; 89:1275-90.

41. Joe B, Vijaykumar M, Lokesh B R. Biological properties of curcumin-cellular and molecular mechanisms of action. Crit Rev Food Sci Nutr 2004; 44:97-111.

42. Fried S K, Bunkin D A, Greenberg A S. Omental and subcutaneous adipose tissues of obese subjects release interleukin-6: depot difference and regulation by glucocorticoid. J Clin Endocrinol Metab 1998; 83:847-50.

43. Hotamisligil G S, Shargill N S, Spiegelman B M. Adipose expression of tumor necrosis factoralpha: direct role in obesity-linked insulin resistance. Science 1993; 259:87-91.

44. Kanda H, Tateya S, Tamori Y, Kotani K, Hiasa K, Kitazawa R, Kitazawa S, Miyachi H, Maeda S, Egashira K, Kasuga M. MCP-1 contributes to macrophage infiltration into adipose tissue, insulin resistance, and hepatic steatosis in obesity. J Clin Invest 2006; 116:1494-505.

45. Yancey P G, Jerome W G. Lysosomal cholesterol derived from mildly oxidized low density lipoprotein is resistant to efflux. J Lipid Res 2001; 42:317-27.

46. Jessup W, Wilson P, Gaus K, Kritharides L. Oxidized lipoproteins and macrophages. Vascul Pharmacol 2002; 38:239-48.

47. Brown A J, Mander E L, Gelissen I C, Kritharides L, Dean R T, Jessup W. Cholesterol and oxysterol metabolism and subcellular distribution in macrophage foam cells. Accumulation of oxidized esters in lysosomes. J Lipid Res 2000; 41:226-37.

48. Tangirala R K, Jerome W G, Jones N L, Small D M, Johnson W J, Glick J M, Mahlberg F H, Rothblat G H. Formation of cholesterol monohydrate crystals in macrophage-derived foam cells. J Lipid Res 1994; 35:93-104.

51. McCullough A J. The clinical features, diagnosis and natural history of nonalcoholic fatty liver disease. Clin Liver Dis 2004; 8:521-533, viii.

52. Clark J M, Diehl A M. Defining nonalcoholic fatty liver disease: implications for epidemiologic studies. Gastroenterology 2003; 124:248-250.

53. Parekh S, Anania F A. Abnormal lipid and glucose metabolism in obesity: implications for nonalcoholic fatty liver disease. Gastroenterology 2007; 132:2191-2207.

54. Bieghs V, Wouters K, van Gorp P J, Gijbels M J, de Winther M P, Binder C J, Lutjohann D, et al. Role of scavenger receptor A and CD36 in diet-induced nonalcoholic steatohepatitis in hyperlipidemic mice. Gastroenterology; 138:2477-2486, 2486 e2471-2473.

55. Yamada Y, Doi T, Hamakubo T, Kodama T. Scavenger receptor family proteins: roles for atherosclerosis, host defence and disorders of the central nervous system. Cell Mol Life Sci 1998; 54:628-640.

56. Karvonen J, Paivansalo M, Kesaniemi Y A, Horkko S. Immunoglobulin M type of autoantibodies to oxidized low-density lipoprotein has an inverse relation to carotid artery atherosclerosis. Circulation 2003; 108:2107-2112.

57. Horkko S, Bird D A, Miller E, Itabe H, Leitinger N, Subbanagounder G, Berliner J A, et al. Monoclonal autoantibodies specific for oxidized phospholipids or oxidized phospholipid-protein adducts inhibit macrophage uptake of oxidized low-density lipoproteins. J Clin Invest 1999; 103:117-128.

58. Tsimikas S, Brilakis E S, Lennon R J, Miller E R, Witztum J L, McConnell J P, Kornman K S, et al. Relationship of IgG and IgM autoantibodies to oxidized low density lipoprotein with coronary artery disease and cardiovascular events. J Lipid Res 2007; 48:425-433.

59. Chou M Y, Fogelstrand L, Hartvigsen K, Hansen L F, Woelkers D, Shaw P X, Choi J, et al. Oxidation-specific epitopes are dominant targets of innate natural antibodies in mice and humans. J Clin Invest 2009; 119:1335-1349.

60. Lutz H U, Binder C J, Kaveri S. Naturally occurring auto-antibodies in homeostasis and disease. Trends Immunol 2009; 30:43-51.

61. Binder C J, Silverman G J. Natural antibodies and the autoimmunity of atherosclerosis. Springer Semin Immunopathol 2005; 26:385-404.

62. Baumgarth N. The double life of a B-1 cell: self-reactivity selects for protective effector functions. Nat Rev Immunol; 11:34-46.

63. Shaw P X, Horkko S, Chang M K, Curtiss L K, Palinski W, Silverman G J, Witztum J L. Natural antibodies with the T15 idiotype may act in atherosclerosis, apoptotic clearance, and protective immunity. J Clin Invest 2000; 105: 1731-1740.

64. Palinski W, Horkko S, Miller E, Steinbrecher U P, Powell H C, Curtiss L K, Witztum J L. Cloning of monoclonal autoantibodies to epitopes of oxidized lipoproteins from apolipoprotein E-deficient mice. Demonstration of epitopes of oxidized low density lipoprotein in human plasma. J Clin Invest 1996; 98:800-814.

65. Binder C J, Horkko S, Dewan A, Chang M K, Kieu E P, Goodyear C S, Shaw P X, et al. Pneumococcal vaccination decreases atherosclerotic lesion formation: molecular mimicry between *Streptococcus pneumoniae* and oxidized LDL. Nat Med 2003; 9:736-743.

66. Wouters K, van Gorp P J, Bieghs V, Gijbels M J, Duimel H, Lutjohann D, Kerksiek A, et al. Dietary cholesterol, rather than liver steatosis, leads to hepatic inflammation in hyperlipidemic mouse models of nonalcoholic steatohepatitis. Hepatology 2008; 48:474-486.

67. Briles D E, Forman C, Hudak S, Claflin J L. Anti-phosphorylcholine antibodies of the T15 idiotype are optimally protective against *Streptococcus pneumoniae*. J Exp Med 1982; 156:1177-1185.

68. Rensen S S, Slaats Y, Driessen A, Peutz-Kootstra C J, Nijhuis J, Steffensen R, Greve J W, et al. Activation of the complement system in human nonalcoholic fatty liver disease. Hepatology 2009; 50:1809-1817.

69. Itabe H, Suzuki K, Tsukamoto Y, Komatsu R, Ueda M, Mori M, Higashi Y, et al. Lysosomal accumulation of oxidized phosphatidylcholine-apolipoprotein B complex in macrophages: intracellular fate of oxidized low density lipoprotein. Biochim Biophys Acta 2000; 1487:233-245.

70. Ehara S, Ueda M, Naruko T, Haze K, Itoh A, Otsuka M, Komatsu R, et al. Elevated levels of oxidized low density lipoprotein show a positive relationship with the severity of acute coronary syndromes. Circulation 2001; 103:1955-1960.

71. Stewart C R, Stuart L M, Wilkinson K, van Gils J M, Deng J, Halle A, Rayner K J, et al. CD36 ligands promote sterile inflammation through assembly of a Toll-like receptor 4 and 6 heterodimer. Nat Immunol; 11:155-161.

72. Platt N, Suzuki H, Kurihara Y, Kodama T, Gordon S. Role for the class A macrophage scavenger receptor in the phagocytosis of apoptotic thymocytes in vitro. Proc Natl Acad Sci USA 1996; 93:12456-12460.

73. Febbraio M, Hajjar D P, Silverstein R L. CD36: a class B scavenger receptor involved in angiogenesis, atherosclerosis, inflammation, and lipid metabolism. J Clin Invest 2001; 108:785-791.

74. Cotena A, Gordon S, Platt N. The class A macrophage scavenger receptor attenuates CXC chemokine production and the early infiltration of neutrophils in sterile peritonitis. J Immunol 2004; 173:6427-6432.

75. Caligiuri G, Khallou-Laschet J, Vandaele M, Gaston A T, Delignat S, Mandet C, Kohler H V, et al. Phosphorylcholine-targeting immunization reduces atherosclerosis. J Am Coll Cardiol 2007; 50:540-546.

76. Binder C J, Chang M K, Shaw P X, Miller Y I, Hartvigsen K, Dewan A, Witztum J L. Innate and acquired immunity in atherogenesis. Nat Med 2002; 8:1218-1226.

77. Chang M K, Bergmark C, Laurila A, Horkko S, Han K H, Friedman P, Dennis E A, et al. Monoclonal antibodies against oxidized low-density lipoprotein bind to apoptotic cells and inhibit their phagocytosis by elicited macrophages: evidence that oxidation-specific epitopes mediate macrophage recognition. Proc Natl Acad Sci USA 1999; 96:6353-6358.

78. Kayo S, Ohsawa M, Ehara S, Naruko T, Ikura Y, Hai E, Yoshimi N, et al. Oxidized low-density lipoprotein levels circulating in plasma and deposited in the tissues: comparison between Helicobacter pylori-associated gastritis and acute myocardial infarction. Am Heart J 2004; 148:818-825.

79. Hartvigsen K, Chou M Y, Hansen L F, Shaw P X, Tsimikas S, Binder C J, Witztum J L. The role of innate immunity in atherogenesis. J Lipid Res 2009; 50 Suppl:S388-393.

80. Chalasani N, Deeg M A, Crabb D W. Systemic levels of lipid peroxidation and its metabolic and dietary correlates in patients with nonalcoholic steatohepatitis. Am J Gastroenterol 2004; 99:1497-1502.

81. James O, Day C. Non-alcoholic steatohepatitis: another disease of affluence. Lancet 1999; 353:1634-1636.

82. Ikura Y, Ohsawa M, Suekane T, Fukushima H, Itabe H, Jomura H, Nishiguchi S, et al. Localization of oxidized phosphatidylcholine in nonalcoholic fatty liver disease: impact on disease progression. Hepatology 2006; 43:506-514.

83. Rensen S S, Slaats Y, Nijhuis J, Jans A, Bieghs V, Driessen A, Malle E, et al. Increased hepatic myeloperoxidase activity in obese subjects with nonalcoholic steatohepatitis. Am J Pathol 2009; 175:1473-1482.

84. Sanyal A J, Campbell-Sargent C, Mirshahi F, Rizzo W B, Contos M J, Sterling R K, Luketic V A, et al. Nonalcoholic steatohepatitis: association of insulin resistance and mitochondrial abnormalities. Gastroenterology 2001; 120: 1183-1192.

85. McClain C J, Mokshagundam S P, Barve S S, Song Z, Hill D B, Chen T, Deaciuc I. Mechanisms of non-alcoholic steatohepatitis. Alcohol 2004; 34:67-79.

86. Sanyal A J, Chalasani N, Kowdley K V, McCullough A, Diehl A M, Bass N M, Neuschwander-Tetri B A, et al. Pioglitazone, vitamin E, or placebo for nonalcoholic steatohepatitis. N Engl J Med; 362:1675-1685.

87. Kang Q, Chen A. Curcumin eliminates oxidized LDL roles in activating hepatic stellate cells by suppressing gene expression of lectin-like oxidized LDL receptor-1. Lab Invest 2009; 89:1275-1290.

88. Joe B, Vijaykumar M, Lokesh B R. Biological properties of curcumin-cellular and molecular mechanisms of action. Crit Rev Food Sci Nutr 2004; 44:97-111.
89. Tangirala R K, Jerome W G, Jones N L, Small D M, Johnson W J, Glick J M, Mahlberg F H, et al. Formation of cholesterol monohydrate crystals in macrophage-derived foam cells. J Lipid Res 1994; 35:93-104.

The invention claimed is:

1. A method for the treatment of a subject suffering from non-alcoholic steatohepatitis liver inflammation; the method comprising:
   administering to the subject a composition that passively or actively immunizes the subject against oxidized low density lipoprotein;
   so as to treat the liver inflammation in the subject as may be determined by a decreased level of tumor necrosis factor, interleukin-1beta, interleukin 6, or monocyte chemoattractant protein-1 in the liver of the subject.

2. The method according to claim 1, wherein the composition passively immunizes the subject against oxidized low density lipoprotein.

3. The method according to claim 2, wherein the composition comprises antibodies against oxidized low density lipoprotein.

4. The method according to claim 1, wherein the composition actively immunizes the subject against oxidized low density lipoprotein.

5. The method according to claim 4, wherein the composition comprises a phosphorylcholine headgroup.

6. The method according to claim 5, wherein the composition comprises a *Streptococcus pneumoniae* antigen.

7. The method according to claim 6, wherein the *Streptococcus pneumoniae* antigen is derived from heat-inactivated *Streptococcus pneumoniae*.

8. A method of treating a subject diagnosed as suffering from non-alcoholic steatohepatitis liver inflammation, the method comprising:
   delivering anti-oxidized low density lipoprotein antibodies or a phosphorylcholine headgroup to the subject,
   so as to treat the subject for liver inflammation as may be determined by a decreased level of tumor necrosis factor, interleukin-1beta, interleukin 6, or monocyte chemoattractant protein-1 in the liver of the subject.

9. The method according to claim 8, comprising administering a composition comprising a *Streptococcus pneumoniae* antigen to the subject.

10. The method according to claim 9, wherein the *S. pneumoniae* antigen is derived from heat-inactivated *S. pneumoniae*.

11. A method for the treatment of liver inflammation in a subject suffering from non-alcoholic steatohepatitis; the method comprising:
   administering to the subject a composition comprising antibodies against oxidized low density lipoprotein,
   so as to treat the liver inflammation in the subject as may be determined by a decreased level of tumor necrosis factor, interleukin-1beta, interleukin 6, or monocyte chemoattractant protein-1 in the liver of the subject.

* * * * *